(12) United States Patent
Lee et al.

(10) Patent No.: US 10,597,685 B2
(45) Date of Patent: Mar. 24, 2020

(54) HOST CELLS AND METHODS FOR OXIDIZING AROMATIC AMINO ACIDS

(71) Applicant: The Regents of the University of California, Oakland, CA (US)

(72) Inventors: Taek Soon Lee, Berkeley, CA (US); Yasuharu Satoh, Sapporo (JP); Jay D. Keasling, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 29 days.

(21) Appl. No.: 14/042,270

(22) Filed: Sep. 30, 2013

(65) Prior Publication Data
US 2014/0134689 A1 May 15, 2014

Related U.S. Application Data

(63) Continuation of application No. PCT/US2012/031025, filed on Mar. 28, 2012.
(Continued)

(51) Int. Cl.
C12N 1/14 (2006.01)
C12N 1/20 (2006.01)
C12P 7/22 (2006.01)
C12N 9/04 (2006.01)
C12N 9/06 (2006.01)
(Continued)

(52) U.S. Cl.
CPC .......... C12P 7/22 (2013.01); C12N 1/14 (2013.01); C12N 1/20 (2013.01); C12N 9/0006 (2013.01); C12N 9/0022 (2013.01); C12N 9/88 (2013.01); C12P 13/001 (2013.01); C12P 13/225 (2013.01); C12P 13/227 (2013.01);
(Continued)

(58) Field of Classification Search
None
See application file for complete search history.

(56) References Cited

U.S. PATENT DOCUMENTS 5,212,082 A * 5/1993 Goldstein et al. ............ 435/190
5,990,094 A 11/1999 Cole et al.
(Continued)

FOREIGN PATENT DOCUMENTS

WO WO 9718319 A1 * 5/1997
WO WO 0206337 A1 * 1/2002
(Continued)

OTHER PUBLICATIONS

GenBank Accession No. AAA40434.1, published Apr. 27, 1993.*
(Continued)

Primary Examiner — Richard C Ekstrom
(74) Attorney, Agent, or Firm — Robin C. Chiang; Lawrence Berkeley National Laboratory

(57) ABSTRACT

The present invention provides for a method of producing an oxidation product of an aromatic amino acid in a genetically modified host cell. The method comprises culturing the genetically modified host cell under a suitable condition such that the culturing results in the genetically modified host cell producing oxidation product of an aromatic amino acid. The host cell comprises an enzyme capable of catalyzing the oxidation of aromatic amino acid. In some embodiments, the host cell is capable of biosynthesizing BH4 or MH4 from GTP.

5 Claims, 14 Drawing Sheets
Specification includes a Sequence Listing.

Related U.S. Application Data

(60) Provisional application No. 61/468,518, filed on Mar. 28, 2011.

(51) Int. Cl.
<table>
<tr><td>C12P 17/10</td><td>(2006.01)</td></tr>
<tr><td>C12P 13/22</td><td>(2006.01)</td></tr>
<tr><td>C12P 17/12</td><td>(2006.01)</td></tr>
<tr><td>C12N 9/88</td><td>(2006.01)</td></tr>
<tr><td>C12P 13/00</td><td>(2006.01)</td></tr>
<tr><td>C12P 17/18</td><td>(2006.01)</td></tr>
</table>

(52) U.S. Cl.
CPC .............. *C12P 17/10* (2013.01); *C12P 17/12* (2013.01); *C12P 17/18* (2013.01)

(56) References Cited

U.S. PATENT DOCUMENTS

| | | | | |
|---|---|---|---|---|
| 6,103,226 | A * | 8/2000 | Kang et al. ............... | 424/93.21 |
| 6,541,219 | B1 * | 4/2003 | Kingsman et al. .......... | 435/69.1 |
| 7,588,757 | B2 * | 9/2009 | Ozawa et al. ............... | 424/93.2 |
| 7,807,421 | B2 | 10/2010 | Yabuta et al. | |
| 2002/0009801 | A1 * | 1/2002 | Falco et al. ................ | 435/320.1 |
| 2002/0028925 | A1 | 3/2002 | Preston et al. | |
| 2002/0172664 | A1 * | 11/2002 | Ozawa et al. ............... | 424/93.2 |
| 2003/0129170 | A1 * | 7/2003 | Iacovitti et al. ........... | 424/93.21 |
| 2003/0198620 | A1 * | 10/2003 | Ozawa et al. ............... | 424/93.2 |
| 2004/0013648 | A1 * | 1/2004 | Kingsman et al. .......... | 424/93.2 |
| 2004/0063175 | A1 | 4/2004 | Abraham et al. | |
| 2005/0196774 | A1 | 9/2005 | Rozzell, Jr. et al. | |
| 2008/0009041 | A1 | 1/2008 | Mizoguchi et al. | |
| 2009/0082286 | A1 * | 3/2009 | Huang et al. .................... | 514/35 |
| 2010/0068775 | A1 * | 3/2010 | Achkar et al. ................ | 435/156 |
| 2010/0143990 | A1 | 6/2010 | Achkar et al. | |
| 2010/0184166 | A1 * | 7/2010 | Sato et al. .................... | 435/122 |
| 2015/0024440 | A1 * | 1/2015 | Knight et al. ............... | 435/121 |
| 2015/0037849 | A1 * | 2/2015 | Knight et al. ............... | 435/108 |

FOREIGN PATENT DOCUMENTS

| WO | WO 2008153094 A1 * | 12/2008 |
|---|---|---|
| WO | WO 2011054976 A2 * | 5/2011 |

OTHER PUBLICATIONS

GenBank Accession No. AAB47157.1, published Feb. 12, 1997.*
GenBank Accession No. BAA14992.2, published Nov. 20, 2008.*
Park et al., "Conversion of 5-hydroxytryptophan into serotonin by tryptophan decarboxylase in plants, *Escherichia coli*, and yeast", Bioscience, Biotechnology and Biochemistry, vol. 72, No. 9, pp. 2456-2458, 2008.*
Leff et al., "In vivo L-DOPA production by genetically modified primary rat fibroblast or 9L gliosarcoma cell grafts via coexpression of GTP cyclohydrolase I with tyrosine hydroxylase", Experimental Neurology, vol. 151, pp. 249-264, 1998.*
Bencsics et al., "Double transduction with GTP cyclohydrolase I and tyrosine hydroxylase is necessary for spontaneous synthesis of L-DOPA by primary fibroblasts", The Journal of Neuroscience, vol. 16, No. 14, pp. 4449-4456, 1996.*
Mandel et al., "Characterization of intrastriatal recombinant adeno-associated virus-mediated gene transfer of human tyrosine hydroxylase and human GTP-cyclohydrolase I in a rat model of Parkinson's disease", The Journal of Neuroscience, vol. 18, No. 11, pp. 4271-4284, 1998.*
Bjorklund et al., "Optimization of continuous in vivo DOPA production and studies on ectopic DA synthesis using rAAV5 vectors in Parkinsonian rats", Journal of Neurochemistry, vol. 111, pp. 355-367, 2009.*
Satoh et al., "Engineering of L-tyrosine oxidation in *Escherichia coli* and microbial production of hydroxytyrosol", Metabolic Engineering, vol. 14, pp. 603-610, 2012.*
Laufs et al., "Retrovirus-mediated double transduction of the GTPCH and PTPS genes allows 6-pyruvoyltetrahydropterin synthase-deficient human fibroblasts to synthesize and release tetrahydrobiopterin", Journal of Neurochemistry, vol. 71, pp. 33-40, 1998.*
Kang et al., "Enhanced production of melatonin by ectopic overexpression of human serotonin N-acetyltransferase plays a role in cold resistance in transgenic rice seedlings", Journal of Pineal Research, vol. 49, pp. 176-182, 2010.*
Park et al., "Production of serotonin by dual expression of tryptophan decarboxylase and tryptamine 5-hydroxylase in *Escherichia coli*", Applied Microbiology and Biotechnology, vol. 89, pp. 1387-1394, 2011.*
Kang et al., "Characterization of rice tryptophan decarboxylases and their direct involvement in serotonin biosynthesis in transgenic rice", Planta, vol. 227, pp. 263-272, 2007.*
Ferry et al., "Characterization and regulation of a CHO cell line stably expressing human serotonin N-acetyltransferase (EC 2.3.1.87)", Cellular and Molecular Life Sciences, vol. 59, pp. 1395-1405, 2002.*
GenBank Accession No. CAA41955.1, published Nov. 3, 1992.*
Thony et al., "Tetrahydrobiopterin biosynthesis, regeneration and functions", Biochemical Journal, vol. 347, pp. 1-16, 2000.*
Kowlessur et al., "Cloning and expression of recombinant human pineal tryptophan hydroxylase in *Escherichia coli*: purification and characterization of the cloned enzyme", Biochimica et Biophysica Acta, vol. 1434, pp. 317-330, 1999.*
International Search Report and Written Opinion for PCT/US2012/031025 dated Aug. 31, 2012.
International Preliminary Report on Patentability for PCT/US2012/031025 dated Mar. 18, 2014.
Moore, Patrick S, Dominici, Paola and Born Voltattorni, Carla. Cloning and expression of pig kidney dopa decarboxylase: comparison of the naturally occurring and recombinant enzymes. Biochem.J (1996) 315, 249-256.
Roh, Jung Hyeob et al. Purification, Cloning, and Three-Dimensional Structure Prediction of Micrococcus luteus FAD-Containing Tyramine Oxidase. Biochemical and Biophysical Res. Communications (2000) 268, 293-297.
Daubner, S. Collette et al. Tyrosine Hydroxylase and Regulation of Dopamine Synthesis. Archives of Biochemistry and Biophysics. (Apr. 1, 2011) 508(1), 1-12.
Fitzpatrick, Paul F. Tetrahydropterin-Dependent Amino Acid Hydroxylases. Annual Review of Biochemistry. (1999) 68, 355-381.
Ikemoto, Kazuhisa et al. (6R)-5,6,7,8-Tetrahydro-L-Monapterin from *Escherichia coli*, a Novel Natural Unconjugated Tetrahydropterin. Journal of Biological Chemistry. (Feb. 2002) 383, 325-330.
Kappock, T. Joseph et al. Pterin-Dependent Amino Acid Hydroxylases. Chemical Reviews. (1996) 96, 2659-2756.
Pribat, Anne et al. FoIX and FoIM Are Essential for Tetrahydromonapterin Synthesis in *Escherichia coli* and Pseudomonas aeruginosa. Journal of Bacteriology. (Jan. 2010) 192(2), 475-482.

\* cited by examiner

A

B

A

B

Transform *E. coli* BLR

HOST CELLS AND METHODS FOR OXIDIZING AROMATIC AMINO ACIDS

CROSS-REFERENCE TO RELATED APPLICATIONS

This application claims priority as a continuation application of PCT International Patent Application No. PCT/US12/31025, filed Mar. 28, 2012, which claims priority to U.S. Provisional Patent Application Ser. No. 61/468,518, filed Mar. 28, 2011, both of which are hereby incorporated by reference in their entireties.

STATEMENT OF GOVERNMENTAL SUPPORT

The invention described and claimed herein was made utilizing funds supplied by the U.S. Department of Energy under Contract No. DE-AC02-05CH11231. The government has certain rights in this invention.

FIELD OF THE INVENTION

The present invention is in the field of production of oxidized products of aromatic amino acids, and in particular host cells that are genetically modified to produce oxidized products of aromatic amino acids.

BACKGROUND OF THE INVENTION

Hydroxylation of aromatic rings is an important reaction used for the preparation of many valuable compounds including L-DOPA for the treatment of Parkinson's disease, benzylisoquinoline alkaloids, and melatonin. Compared with chemical reaction which frequently uses metallic oxidants in organic solvent, hydroxylation of aromatic ring by microorganisms is an interesting and promising method to synthesize the desired products in a single-step with a high regioselectivity and under mild conditions. Microbial aromatic hydroxylation is involved in the aerobic metabolism of aromatic compounds and mostly performed by oxygenases and tyrosinases during the degradation process either to relieve the toxicity or to metabolize them into organic acid to use as carbon sources.

Tyrosinase is an oxidoreductase belongs to type-3 copper protein which includes hemocyanins as an oxygen carrier. (Olivares, 2009; Robb, 1984) This enzyme involves multiple oxidation reaction of L-tyrosine using molecular oxygen as oxidant; the first oxidation step is o-hydroxylation of L-tyrosine to L-DOPA and is known to be the slowest step, and the second oxidation step is the production of o-quinone from o-diphenol which is fast and followed by non-enzymatic reaction to dopachrome, a colored intermediate to melanin pathway. Microbial conversion of tyrosine to L-DOPA is slow process, and the over-oxidation to ortho-quinone is hard to avoid when tyrosinase is used. The use of reducing agent such as ascorbic acid adds more step for the purification of the product from fermentation broth.

L-DOPA is an important compound to living cells, especially in animal since it is used as a precursor for many neurotransmitters, and in animal brain, L-DOPA was synthesized by tyrosine hydroxylase (TH) with tetrahydrobiopterin (BH4) as a cofactor. (Kappock, Chem. Rev. 1996; Fitzpatrick, Ann Rev Biochem 1999; Daubner, Arch Biochem Biophys 2011) The use of pterin cofactor during the oxidation step is unique feature of TH and related enzyme such as phenylalanine hydroxylase (PAH) and tryptophan hydroxylase (TPH), (Pribat, J. Bacteriol. 2010) and this helps to prevent over-oxidation of L-tyrosine to o-quinone product which is a problem in microbial L-DOPA production by tyrosinase (Maass, 2003). However, the application of TH enzyme to microbial metabolic engineering has not been reported due to the unavailability of the coenzyme BH4 in microbes. BH4 is a unique co-factor found in animal and no bacterial system has been reported to use BH4 for biosynthesis of L-DOPA or related metabolites.

SUMMARY OF THE INVENTION

The present invention provides for a method of producing an oxidation product of an aromatic amino acid in a genetically modified host cell. The method comprises culturing the genetically modified host cell under a suitable condition such that the culturing results in the genetically modified host cell producing oxidation product of an aromatic amino acid. The host cell comprises an enzyme capable of catalyzing the oxidation of aromatic amino acid. In some embodiments of the invention, the aromatic amino acid is tyrosine or tryptophan.

The present invention provides for a method for the oxidation of L-tyrosine to L-DOPA in a host cell, such as *E. coli*, using mouse tyrosine hydroxylase (Iwata, Biochem Biophys Res Comm 1992; hereby incorporated by reference) without or minimized overoxidation to o-quinone.

The present invention also provides for a genetically modified host cell useful for the methods of the present invention.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
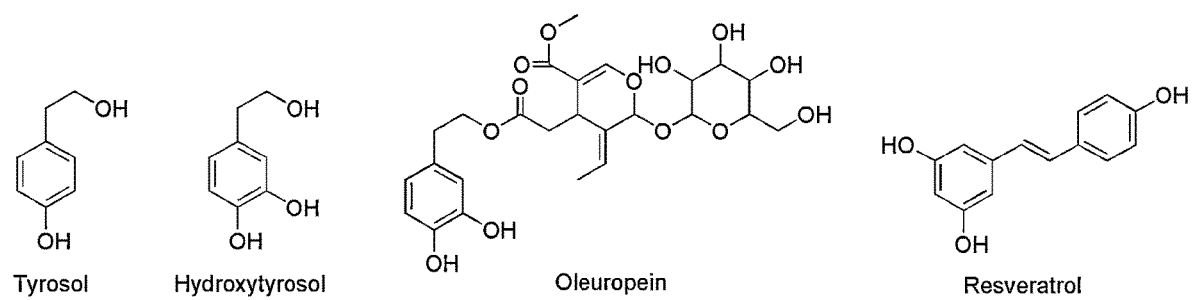
FIG. 1 shows the chemical of the antioxidants: tyrosol, hydroxytyrosol, ester of hydroxytyrosol, and resveratrol. Tyrosol, Hydroxytyrosol, Oleuropein (elenolic acid ester of hydroxytyrosol), and Resveratrol are naturally occurring antioxidants.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "host microorganism" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

Producing Oxidation Products from an Aromatic Amino Acid

Figure 2:
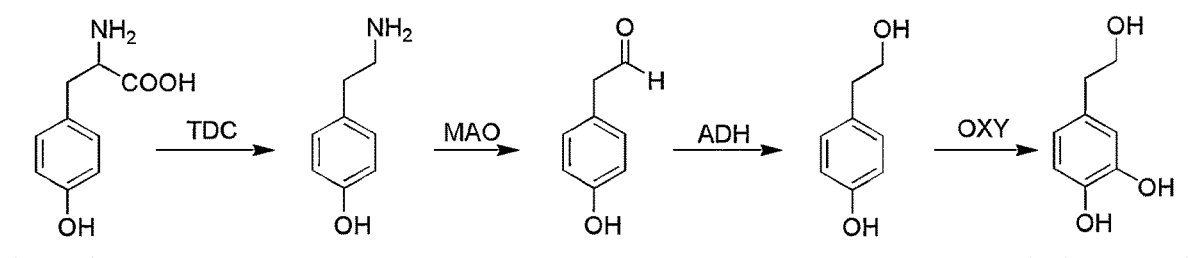
FIG. 2 shows the biosynthesis of hydroxytyrosol (with hydroxylation as the last step) from tyrosine. Biosynthetic hydroxytyrosol production from L-tyrosine with hydroxylation as the last step. TDC: tyrosine decarboxylase, MAO: monoamine oxidase, ADH: alcohol dehydrogenase, OXY: monooxygenase
Figure 3:
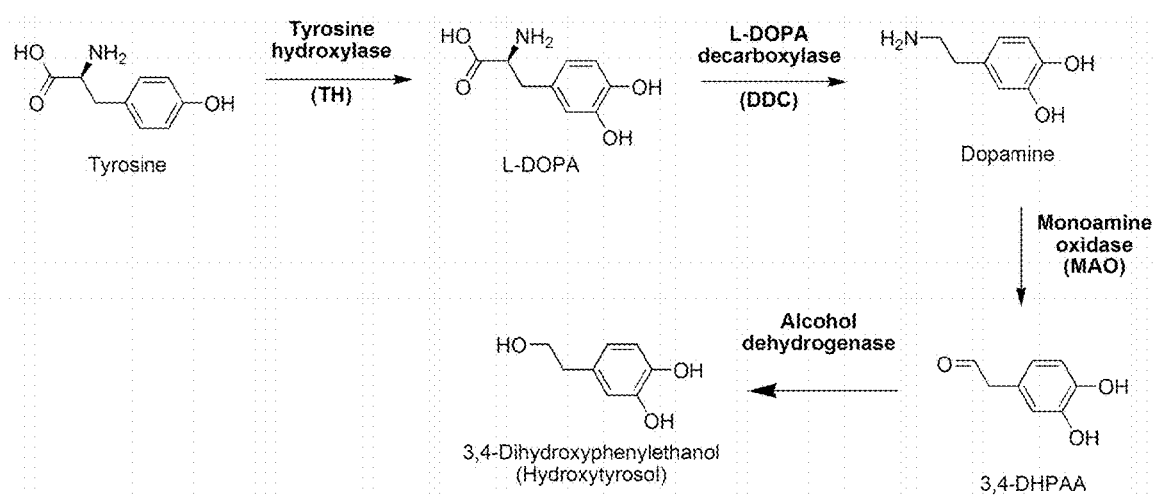
FIG. 3 shows the biosynthetic pathway of (A) hydroxytyrosol and (B) melatonin. Tyrosine and tryptophan can be biosynthesized from a suitable carbon source, such as glucose. "TH" is tyrosine hydroxylase. "DDC" is L-DOPA decarboxylase. "MAO" is monoamine oxidase.
Figure 3:
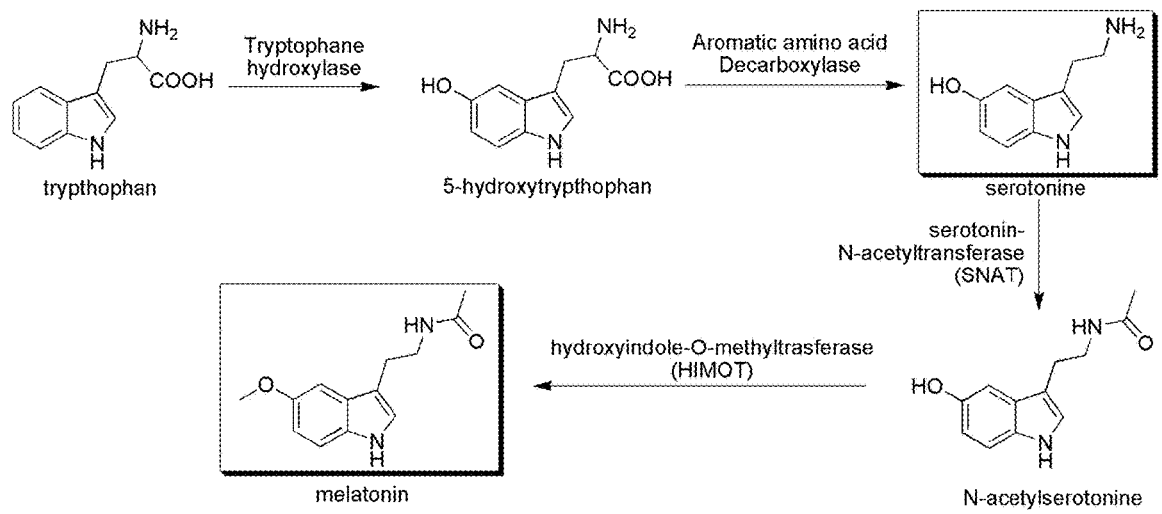

Hydroxytyrosol is one of the most powerful antioxidants found in olive oil as the form of its elenolic acid ester oleuropein (FIG. 1). Hydroytyrosol has powerful antioxidant properties and its oxygen radical absorbance capacity (ORAC) is about 50% higher than resveratrol, an antioxidant found in red wine. Hydroxytyrosol is marketed under the brandnames Hytolive® (Genosa I+D, S. A., Malaga, Spain) and Hydrox® (Creagri Inc., Hayward, Calif.). Currently most hydroxytyrosol is produced by the hydrolysis of olive extracts (that contain elenolic acid ester of hydroxytyrosol, oleuopein), although several methods have been developed to produce the hydroxytyrosol by chemical synthesis and enzymatic conversion. Hydroxytyrosol is also a metabolite of neurotransmitter dopamine, and this compound can be made biosynthetically by the pathway described in FIG. 2A.

The present invention provides for a method of producing one or more oxidation products of an aromatic amino acid in a genetically modified host cell. The method comprises culturing the genetically modified host cell under a suitable condition such that the culturing results in the genetically modified host cell producing one or more oxidation products of an aromatic amino acid. The host cell comprises an enzyme capable of catalyzing the oxidation of aromatic amino acid.

In some embodiments of the invention, the aromatic amino acid is tyrosine or tryptophan. In some embodiments of the invention, the aromatic amino acid is tyrosine and the one or more oxidation products are L-DOPA, dopamine, 3,4-dihydroxyphenylacetaldehyde, 3,4-dihydroxypehletha- nol (hydroxytyrosol), reticuline, thebaine, and/or morphine. In some embodiments of the invention, the aromatic amino acid is tryptophan and one or more oxidation products are 5-hydroxytryptophan, serotonin, and/or melatonin.

In some embodiments of invention, for the method for producing one or more oxidation products of an aromatic amino acid in a genetically modified host cell, the method comprises: culturing a genetically modified host cell under a suitable condition, wherein the genetically modified host cell comprises one or more enzymes capable of catalyzing the oxidation of the aromatic amino acid into the one or more oxidation products, such that the culturing results in the genetically modified host cell producing the one or more oxidation products.

In some embodiments of invention, for the method for producing one or more oxidation products of tyrosine in a genetically modified host cell, the method comprises: culturing a genetically modified host cell under a suitable condition, wherein the genetically modified host cell comprises one or more enzymes capable of catalyzing the oxidation of tyrosine into L-DOPA, dopamine, 3,4-dihydroxyphenylacetaldehyde, 3,4-dihydroxypehylethanol (hydroxytyrosol), reticuline, thebaine, and/or morphine, such that the culturing results in the genetically modified host cell producing L-DOPA, dopamine, 3,4-dihydroxyphenylacetaldehyde, 3,4-dihydroxypehylethanol (hydroxytyrosol), reticuline, thebaine, and/or morphine.

In some embodiments of invention, for the method for producing one or more oxidation products of tryptophan in a genetically modified host cell, the method comprises: culturing a genetically modified host cell under a suitable condition, wherein the genetically modified host cell comprises one or more enzymes capable of catalyzing the oxidation of tryptophan into 5-hydroxytryptophan, serotonin, and/or melatonin, such that the culturing results in the genetically modified host cell producing 5-hydroxytryptophan, serotonin, and/or melatonin.

In some embodiments of invention, the method comprises culturing the genetically modified host cell with exogenously provided aromatic amino acid, or a suitable carbon source. When the method comprises culturing the genetically modified host cell with a suitable carbon source, the genetically modified host cell is capable of synthesizing the aromatic amino acid using a native biosynthetic pathway or a heterologous biosynthetic pathway residing on one or more nucleic acids in the host cell, wherein the one or more nucleic acids are on one or more vectors or stably integrated into a host cell chromosome. Suitable carbon sources which the host cell is capable of uptaking and metabolizing. Such carbon sources include but are not limited to sugars, such as monosaccharides, such as glucose.

In some embodiments of invention, for the method for producing one or more oxidation products of an aromatic amino acid in a genetically modified host cell, the method comprises: (a) introducing a nucleic acid construct encoding an enzyme capable of catalyzing the oxidation of the aromatic amino acid into a genetically modified host cell; and (b) culturing the genetically modified host cell under a suitable condition such that the enzyme is expressed in the host cell; such that the culturing results in the genetically modified host cell producing one or more oxidation products.

The present invention provides for a genetically modified host cell capable of producing one or more oxidation products of an aromatic amino acid, comprising or capable of expressing one or more heterologous enzymes capable of catalyzing the oxidation of aromatic amino acid. In some embodiments, the aromatic amino acid is tyrosine or tryptophan. In some embodiments, the aromatic amino acid is tyrosine and the one or more oxidation products are L-DOPA, dopamine, 3,4-dihydroxyphenylacetaldehyde, 3,4-dihydroxypehylethanol (hydroxytyrosol), reticuline, thebaine, and/or morphine. In some embodiments, the aromatic amino acid is tryptophan and one or more oxidation products are 5-hydroxytryptophan, serotonin, and/or melatonin.

In some embodiments of invention, the one or more enzymes are capable of catalyzing the oxidation of tyrosine into L-DOPA, dopamine, 3,4-dihydroxyphenylacetaldehyde, 3,4-dihydroxypehylethanol (hydroxytyrosol), reticuline, thebaine, and/or morphine, such that the culturing the host cell results in the host cell producing L-DOPA, dopamine, 3,4-dihydroxyphenylacetaldehyde, 3,4-dihydroxypehylethanol (hydroxytyrosol), reticuline, thebaine, and/or morphine.

In some embodiments of invention, the one or more enzymes are capable of catalyzing the oxidation of tryptophan into 5-hydroxytryptophan, serotonin, and/or melatonin, such that the culturing the host cell results in the host cell producing 5-hydroxytryptophan, serotonin, and/or melatonin.

In some embodiments, the host cell comprises or is capable of expressing TDC, MAO, ADH, and/or OXY, or homologous enzymes thereof, wherein one or more of the enzymes are overproduced compared to the unmodified host cell or one or more of the enzymes is heterologous to the host cell. In some embodiments, the host cell is capable of endogenously producing tyrosine, either by native enzymes of the tyrosine biosynthetic pathway, or a heterologous tyrosine biosynthetic pathway introduced into the host cell.

In some embodiments, the host cell comprises or is capable of expressing TH, DDC, MAO, and/or alcohol dehydrogenase, or homologous enzymes thereof, wherein one or more of the enzymes are overproduced compared to the unmodified host cell or one or more of the enzymes is heterologous to the host cell. In some embodiments, the host cell is capable of endogenously producing tyrosine, either by native enzymes of the tyrosine biosynthetic pathway, or a heterologous tyrosine biosynthetic pathway introduced into the host cell.

In some embodiments, the host cell comprises or is capable of expressing heterologous TH (such as mouse TH), heterologous DDC (such as pig DDC), and/or heterologous MAO (such as *M. luteus* MAO), or homologous enzymes thereof.

In some embodiments, the host cell comprises or is capable of expressing tryptophan hydroxylase, aromatic amino acid decarboxylase, SNAT, and/or HIMOT, or homologous enzymes thereof, wherein one or more of the enzymes are overproduced compared to the unmodified host cell or one or more of the enzymes is heterologous to the host cell. In some embodiments, the host cell is capable of endogenously producing tryptophan, either by native enzymes of the tryptophan biosynthetic pathway, or a heterologous tryptophan biosynthetic pathway introduced into the host cell.

In some embodiments, the host cell natively comprises a nucleic acid encoding an enzyme capable of catalyzing phenylacetaldehyde dehydrogenase into 3,4-dihydroxyphenyl acetate (3,4-DHPA), such as the enzyme phenylacetaldehyde dehydrogenase, wherein the host cell is reduced in the expression of the enzyme. When the host cell is *E. coli*, the enzyme is phenylacetaldehyde dehydrogenase encoded by the feaB gene. The reduced expression can be the result of a mutation that reduced expression or reduces enzymatic activity of the enzyme. An example of such a mutation is a truncated or deleted gene, such as a knock out mutation.

Figure 8:
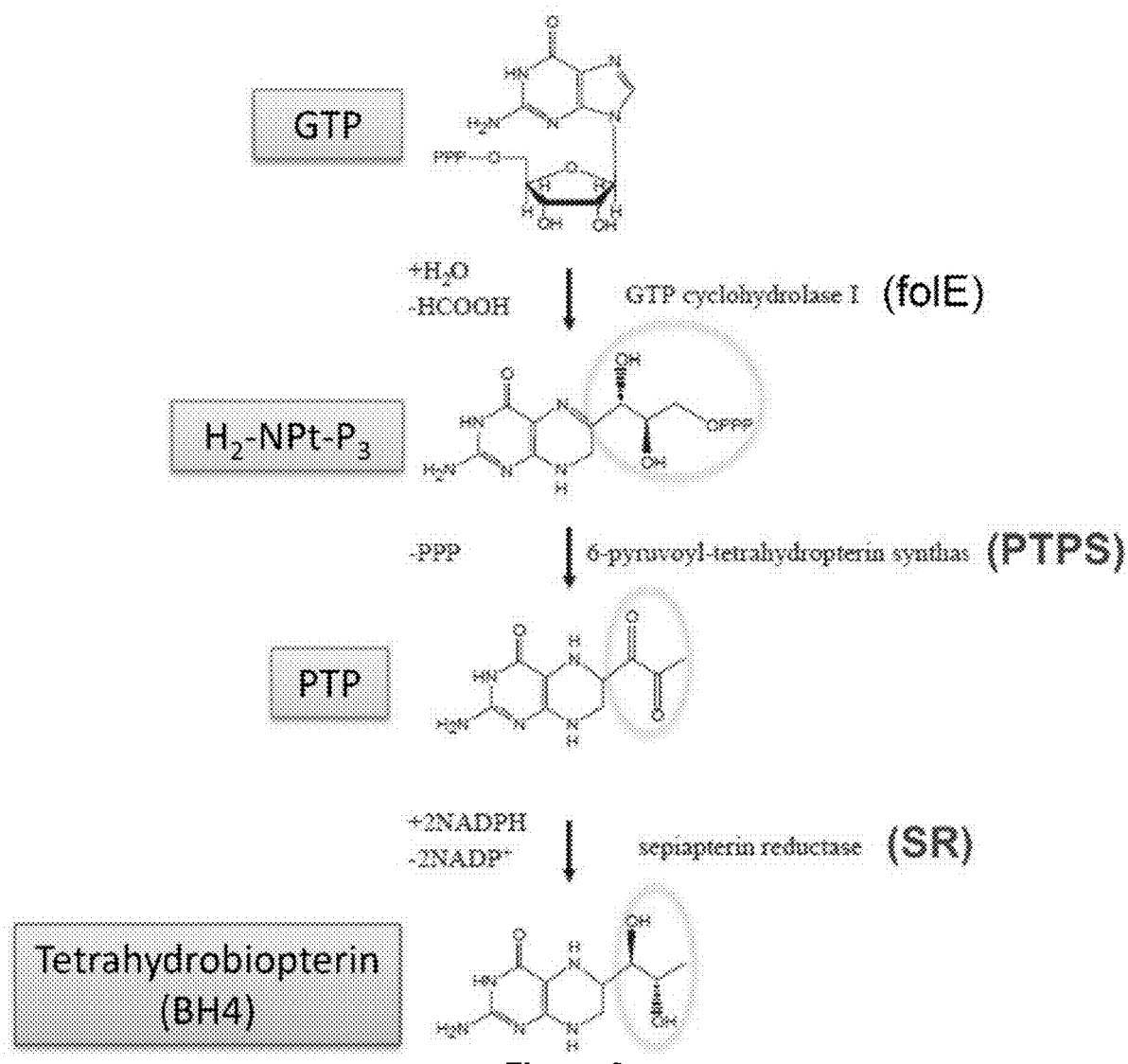
FIG. 8 shows the biosynthesis of BH4 from GTP.
Figure 9:
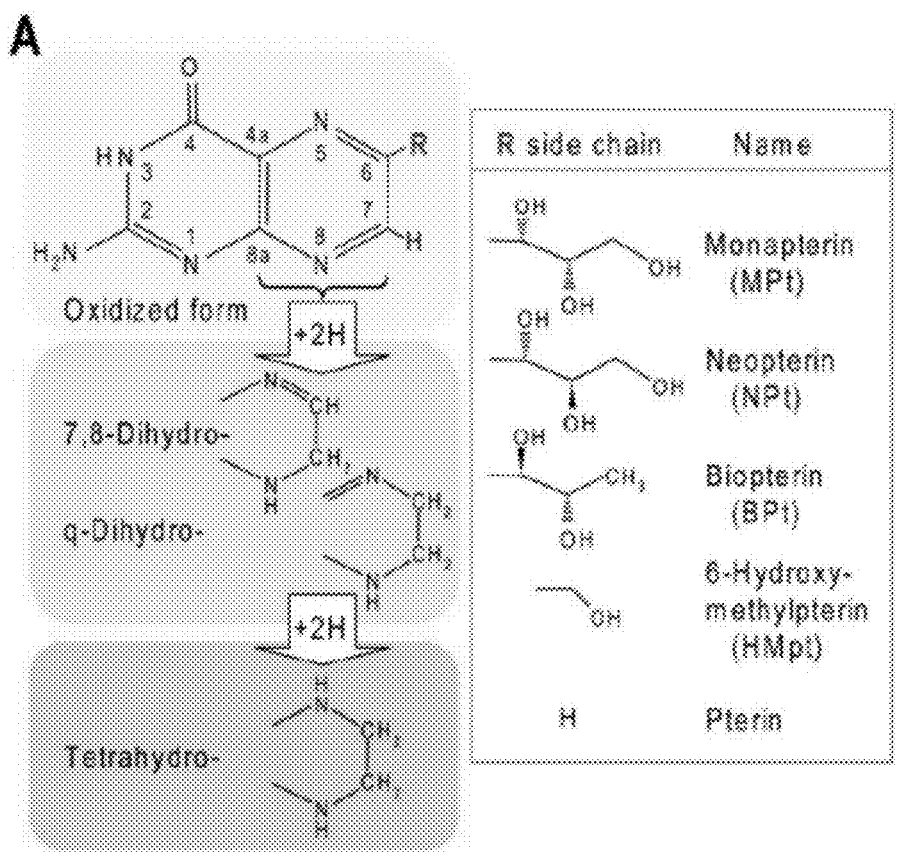
FIG. 9 shows (A) pterin structures, and (B) the biosynthetic pathway for BH4 and MH4 from GTP. Phenylalanine hydrolase (PAH) requires MH4. folX and folX are essential for MH4 biosynthesis.
Figure 9:
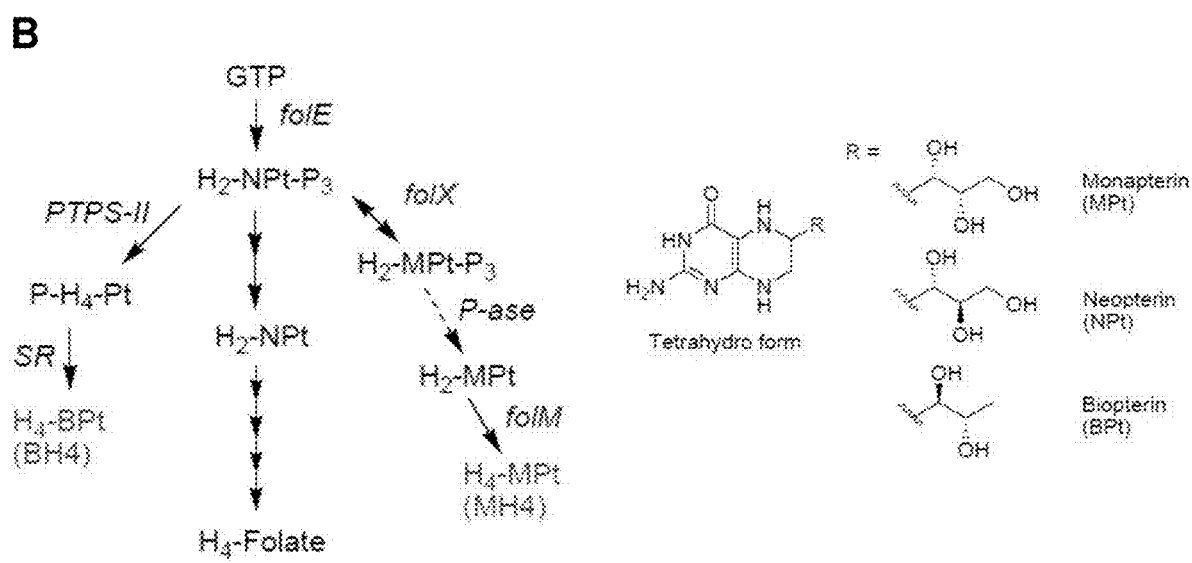

Tetrahydrobiopterin (BH4) is a cofactor found in animals and is widely used in neurotransmitter biosynthesis. BH4 is heterologous to bacteria. The biosynthesis of BH4 from GTP is shown in FIGS. 8 and 9. One means to have a host cell synthesize BH4 is to have the host cell comprise the enzymes GTP cyclohydrolase I (folE), 6-pyruvoyl-tetrahydropterin synthase (PTPS), and sepiapterin reductase (SR), or homologous enzymes thereof. In the present invention, whenever BH4 is required, BH4 can be substituted or replaced with MH4. The biosynthesis of MH4 from GTP is shown in FIG. 9. One means to have a host cell synthesize MH4 is to have the host cell comprise the enzymes GTP cyclohydrolase I (folE), folX, P-ase, and folM, or homologous enzymes thereof.

Tyrosine hydroxylase and tryptophan hydroxylase are enzymes that use tetrahydrobiopterin (BH4) in the catalysis of tyrosine and tryptophan into L-DOPA and 5-hydroxytryptophan, respectively. Pterin-4-alpha-carbinolamine dehydratase (PCD) and dihydropteridine reductase (DHPR) are capable of catalyzing the reactions for BH4 regeneration (see FIG. 4). In some embodiments of invention, when the genetically modified host cell comprises tyrosine hydroxylase or tryptophan hydroxylase, the host cell further comprises pterin-4-alpha-carbinolamine dehydratase (PCD), or a homologous enzyme thereof, and dihydropteridine reductase (DHPR), or a homologous enzyme thereof. In some embodiments of invention, when the genetically modified host cell does not naturally synthesize BH4, the host cell further comprises GTP cyclohydrolase I (folE), 6-pyruvoyl-tetrahydropterin synthase (PTPS), and sepiapterin reductase (SR), or one or more homologous enzymes thereof.

In some embodiments of invention, the method further comprises the step of recovering the produced one or more oxidation products, wherein the recovering step is concurrent or subsequent to the culturing step.

Enzymes, and Nucleic Acids Encoding Thereof.

A homologous enzyme is an enzyme that has a polypeptide sequence that is at least 70%, 75%, 80%, 85%, 90%, 95% or 99% identical to any one of the enzymes described in this specification or in an incorporated reference. The homologous enzyme retains amino acids residues that are recognized as conserved for the enzyme. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof.

A suitable tyrosine hydroxylase or tyrosine 3-monooxygenase is mouse tyrosine hydroxylase (NP_033403), or a homologous enzyme thereof, which has the following amino acid sequence:

(SEQ ID NO: 1)

```
  1 mptpsasspq pkgfrrayse qdtkqaeavt sprfigrrqs liedarkere aaaaaaaaav
 61 asaepgnple avvfeerdgn avlnllfslr gtkpsslsra lkvfetfeak ihhletrpaq
121 rplagsphle yfvrfevpsg dlaallssvr rvsddvrsar edkvpwfprk vseldkchhl
181 vtkfdpdldl dhpgfsdqay rqrrkliaei afqykqgepi phveytkeei atwkevyatl
241 kglyathacr ehleafqlle rycgyredsi pqledvshfl kertgfqlrp vagllsardf
301 laslafrvfq ctqyirhass pmhspepdcc hellghvpml adrtfaqfsq diglaslgas
```

```
361 deeieklstv ywftvefglc kqngelkayg agllssygel lhslseepev rafdpdtaav 421 qpyqdqtyqp vyfvsesfsd akdklrnyas riqrpfsvkf dpytlaidvl dsphtirrsl 481 egvqdelhtl tqalsais
```

A suitable tryptophan hydroxylase or tryptophan 5-hydroxylase is human TPH1 (NP004170), or a homologous enzyme thereof, which has the following amino acid sequence:

```
                                              (SEQ ID NO: 2)
MIEDNKENKDHSLERGRASLIFSLKNEVGGLIKALKIFQEKHVNLLHIES

RKSKRRNSEFEIFVDCDINREQLNDIFHLLKSHTNVLSVNLPDNFTLKED

GMETVPWFPKKISDLDHCANRVLMYGSELDADHPGFKDNVYRKRRKYFAD

LAMNYKHGDPIPKVEFTEEEIKTWGTVFQELNKLYPTHACREYLKNLPLL

SKYCGYREDNIPQLEDVSNFLKERTGFSIRPVAGYLSPRDFLSGLAFRVF

HCTQYVRHSSDPFYTPEPDTCHELLGHVPLLAEPSFAQFSQEIGLASLGA

SEEAVQKLATCYFFTVEFGLCKQDGQLRVFGAGLLSSISELKHALSGHAK

VKPFDPKITCKQECLITTFQDVYFVSESFEDAKEKMREFTKTIKRPFGVK

YNPYTRSIQILKDTKSITSAMNELQHDLDVVSDALAKVSRKPSI
```

Another suitable tryptophan hydroxylase is human TPH2 (NP775489), or a homologous enzyme thereof, which has the following amino acid sequence:

```
                                              (SEQ ID NO: 3)
MQPAMMMFSSKYWARRGFSLDSAVPEEHQLLGSSTLNKPNSGKNDDKGNK

GSSKREAATESGKTAVVFSLKNEVGGLVKALRLFQEKRVNMVHIESRKSR

RRSSEVEIFVDCECGKTEFNELIQLLKFQTTIVTLNPPENIWTEEEELED

VPWFPRKISELDKCSHRVLMYGSELDADHPGFKDNVYRQRRKYFVDVAMG

YKYGQPIPRVEYTEEETKTWGVVFRELSKLYPTHACREYLKNFPLLTKYC

GYREDNVPQLEDVSMFLKERSGFTVRPVAGYLSPRDFLAGLAYRVFHCTQ

YIRHGSDPLYTPEPDTCHELLGHVPLLADPKFAQFSQEIGLASLGASDED

VQKLATCYFFTIEFGLCKQEGQLRAYGAGLLSSIGELKHALSDKACVKAF

DPKTTCLQECLITTFQEAYFVSESFEEAKEKMRDFAKSITRPFSVYFNPY

TQSIEILKDTRSIENVVQDLRSDLNTVCDALNKMNQYLGI
```

A suitable pterin-4-alpha-carbinolamine dehydratase (PCD) is human PCD (NP_000272), or a homologous enzyme thereof, which has the following amino acid sequence:

```
                                              (SEQ ID NO: 4)
  1 magkahrlsa eerdqllpnl ravgwneleg rdaifkqfhf kdfnrafgfm trvalqaekl 61 dhhpewfnvy nkvhitlsth ecaglserdi nlasfieqva vsmt
```

A suitable dihydropteridine reductase (DHPR) is human DHPR (P09417), or a homologous enzyme thereof, which has the following amino acid sequence:

```
                                              (SEQ ID NO: 5)
  1 maaaaaagea rrvlvyggrg algsrcvqaf rarnwwvasv dvveneeasa siivkmtdsf 61 teqadqvtae vgkllgeekv dailcvaggw aggnaksksl fkncdlmwkq siwtstissh 121 latkhlkegg lltlagakaa ldgtpgmigy gmakgavhql cqslagknsg mppgaaaiav 181 lpvtldtpmn rksmpeadfs swtpleflve tfhdwitgkn rpssgsliqv vttegrtelt 241 payf
```

A suitable L-DOPA decarboxylase (DDC) is pig DDC, or a homologous enzyme thereof, which has the following nucleotide (SEQ ID NO:6) and amino acid (SEQ ID NO:7) sequences:

```
-10                            GAATTCACATATGAATGCCAGCGATTTC
                                         M  N  A  S  D  F      6

19 CGTCGACGCGGCAAAGAAATGGTGGATTACATGGCGGATTACCTGGAAGGCATCGAAGGT
     R  R  R  G  K  E  M  V  D  Y  M  A  D  Y  L  E  G  I  E  G   26

79 CGTCAGGTGTACCCGGATGTGCAGCCGGGGTACCTGCGTCCGCTGATCCCGGCGACCGCC
     R  Q  V  Y  P  D  V  Q  P  G  Y  L  R  P  L  I  P  A  T  A   46

139 CCGCAGGAACCGGATACCTTCGAAGATATCCTGCAGGATGTGGAAAAAATCATCATGCCG
     P  Q  E  P  D  T  F  E  D  I  L  Q  D  V  E  K  I  I  M  P   66
```

```
-continued
199 GGGGTGACCCACTGGCACAGCCCGTACTTCTTCGCGTACTTCCCGACCGCCAGCAGCTAC
     G  V  T  H  W  H  S  P  Y  F  F  A  Y  F  P  T  A  S  S  Y      86

259 CCGGCGATGCTGGCGGATATGCTGTGCGGTGCGATCGGATGCATCGGTTTCAGCTGGGCG
      P  A  M  L  A  D  M  L  C  G  A  I  G  C  I  G  F  S  W  A    106

319 GCTAGCCCGGCGTGCACCGAACTCGAGACCGTGATGATGGATTGGCTGGGCAAAATGCTC
      A  S  P  A  C  T  E  L  E  T  V  M  M  D  W  L  G  K  M  L    126

379 CAGCTTCCGGAAGCGTTCCTGGCGGGCGAAGCCGGTGAAGGCGGCGGCGTGATCCAGGGT
      Q  L  P  E  A  F  L  A  G  E  A  G  E  G  G  G  V  I  Q  G    146

439 AGCGCCAGCGAAGCCACCCTGGTGGCGCTGCTGGCGGCGCGTACCAAAGTGGTGCGACGT
      S  A  S  E  A  T  L  V  A  L  L  A  A  R  T  K  V  V  R  R    166

499 CTGCAAGCGGCGAGCCCGGGCCTGACCCAGGGCGCGGTGCTGGAAAAACTAGTGGCGTAC
      L  Q  A  A  S  P  G  L  T  Q  G  A  V  L  E  K  L  V  A  Y    186

559 GCGAGTGATCAGGCGCACAGCAGCGTGGAACGTGCCGGCCTGATCGGCGGCGTGAAACTG
      A  S  D  Q  A  H  S  S  V  E  R  A  G  L  I  G  G  V  K  L    206

619 AAAGCGATCCCGAGCGATGGCAAATTCGCGATGCGTGCGAGCGCGCTGCAGGAGGCCCTG
      K  A  I  P  S  D  G  K  F  A  M  R  A  S  A  L  Q  E  A  L    226

679 GAGAGAGACAAGGCTGCCGGCCTGATTCCTTTCTTCGTGGTGGCTACGCTGGGGACCACA
      E  R  D  K  A  A  G  L  I  P  F  F  V  V  A  T  L  G  T  T    246

739 TCGTGCTGCTCCTTTGACAATCTCTTAGAAGTGGGACCCATCTGTCACGAAGAGGACATA
      S  C  C  S  F  D  N  L  L  E  V  G  P  I  C  H  E  E  D  I    266

799 TGGCTGCACGTGGATGCTGCCTACGCAGGCAGTGCCTTCATCTGCCCTGAGTTCCGGCAC
      W  L  H  V  D  A  A  Y  A  G  S  A  F  I  C  P  E  F  R  H    286

859 CTGCTGAATGGAGTGGAGTTTGCAGATTCATTTAACTTTAATCCCCACAAATGGCTCTTG
      L  L  N  G  V  E  F  A  D  S  F  N  F  N  P  H  K  W  L  L    306

919 GTGAATTTTGACTGCTCGGCTATGTGGGTGAAAAGGAGAACGGACCTGACTGGAGCCTTC
      V  N  F  D  C  S  A  M  W  V  K  R  R  T  D  L  T  G  A  F    326

979 AAATTGGACCCCGTGTACTTAAAGCACAGCCACCAGGGCTCGGGGCTTATCACGGACTAC
      K  L  D  P  V  Y  L  K  H  S  H  Q  G  S  G  L  I  T  D  Y    346

1039 AGGCACTGGCAGCTGCCACTGGGTCGGCGATTCCGGTCCCTGAAAATGTGGTTTGTTTTT
       R  H  W  Q  L  P  L  G  R  R  F  R  S  L  K  M  W  F  V  F   366

1099 AGGATGTACGGAGTCAAGGGACTGCAGGCCTATATCCGAAGCACGTGCAGCTGTCTCAT
       R  M  Y  G  V  K  G  L  Q  A  Y  I  R  K  H  V  Q  L  S  H   386

1159 GAGTTTGAGGCATTTGTGCTTCAGGATCCACGCTTTGAAGTCTGTGCCGAAGTCACCCTG
       E  F  E  A  F  V  L  Q  D  P  R  F  E  V  C  A  E  V  T  L   406

1219 GGGCTGGTGTGTTTCCGGCTGAAGGGCTCCGACGGACTGAATGAAGCGCTTCTGGAAAGG
       G  L  V  C  F  R  L  K  G  S  D  G  L  N  E  A  L  L  E  R   426

1279 ATAAACAGCGCCAGGAAAATCCACTTGGTTCCCTGTCGCCTGAGGGGCCAGTTCGTGCTG
       I  N  S  A  R  K  I  N  L  V  P  C  R  L  R  G  Q  F  V  L   446

1339 CGGTTCGCCATCTGCTCGCGCAAGGTGGAGTCGGGCCACGTGCGGCTGGCCTGGGAGCAC
       R  F  A  I  C  S  R  K  V  E  S  G  H  V  R  L  A  W  E  H   466

1399 ATCCGAGGGCTGGCGGCCGAGCTGCTGGCCGCGGAGGAGGGAAAGGCAGAGATCAAAAGT
       I  R  G  L  A  A  E  L  L  A  A  E  E  G  K  A  E  I  K  S   486

1459 TGAAGTGCCCTGAAGAGCAGAATCGGAGGAGACGCGTCGTCCCCGCTCCGAGGCGTAGAG
       *

1519 CCTGCAATGGTCCCCCCAGTTCTTTAGCCCACGTTCTCCAGAAAGAAGCTTGTGCCTACG

1579 TCTGACCAGCCTCTCAGCAATGAAGAAGTATTATTTGCTCTTTGAAAAGTTAATCCCAGT

1639 GGAGACAGCTTTTACTCTTTATTTGGCTGTGATTGTTTGTTGATTAAAACATCATAGGTT

1699 TCTGCATCCTTGAAGTTGTCAGCGGTGGTCCACTTTCCGGGGCAACCTATGCTGATGGGA

1759 TTTGAGATGATACCCGTGGTCTTTAAATTACTCTGTCCTGTGGCTTATGCTTAATAAATG

1819 ATGTGAAGTGTAAAAAAAAAAAAAAAAAAAA
```

A suitable monoamine oxidase (MAO) is *Micrococcus luteus* MAO (ACS30544.1), or a homologous enzyme thereof, which has the following amino acid sequence:

```
                                                          (SEQ ID NO: 8)
  1 mttapatagr errtsdvvvi gagpaglmaa rtakaqglsv tvlearrrvg grtwnglveg 61 adgkdhfiei ggqwispdqt rlislveelg lptfsrfrdg rnvyvdprge rhvydgldfp 121 vaektdremd rliakidelt aeidaaapwe hpraaeldti sfrhwleqes ddpeaidnvs 181 iyiasgmltk pshtfsmlqa llmaasagsf rnlvdedfil dkrveggmqs vsltmaaelg 241 ddvvlgqpvr tlrwaepdps tadekngvaa dvrngvandg aagdvvaltd dyevharyav 301 lavppnlysr isfeppmpre qqiahqhism glvikvhavy etpfwreegl sgtcfgggrl 361 vqeiydntnr genlaggapg eedphgtlvg fvsdvyaeqm walpeeerka ailgamaeyl 421 gprtlepiaf flsdmaaeew trgayatsyd lgglsrwghl qnrptgpihy acsdiaaegy 481 qhvdgairmg eaaalaiaer eatdagqptg
```

The nucleic acid constructs of the present invention comprise nucleic acid sequences encoding one or more of the subject enzymes. The nucleic acid of the subject enzymes are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) *Tet. Lett.* 521:719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683,195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *E. coli*. See Shine et al. (1975) *Nature* 254:34 and Steitz, in Biological Regulation and Development: Gene Expression (ed. R. F. Goldberger), vol. 1, p. 349, 1979, Plenum Publishing, N.Y.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. An example includes lactose promoters (LacI repressor protein changes conformation when contacted with lactose, thereby preventing the LacI repressor protein from binding to the operator). Another example is the tac promoter. (See deBoer et al. (1983) *Proc. Natl. Acad. Sci. USA,* 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. For example, one method for transforming *E. coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequencers) provides the ability to transfect host microorganisms. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

The host cell is transformed with at least one expression vector. When only a single expression vector is used (without the addition of an intermediate), the vector will contain all of the nucleic acid sequences necessary.

Once the host cell has been transformed with the expression vector, the host cell is allowed to grow. For microbial hosts, this process entails culturing the cells in a suitable medium. It is important that the culture medium contain an excess carbon source, such as a sugar (e.g., glucose) when an intermediate is not introduced. In this way, cellular production of aromatic amino acid ensured. When added, the intermediate is present in an excess amount in the culture medium.

As the host cell grows and/or multiplies, expression of the enzymes necessary for producing the oxidation product(s) is affected. Once expressed, the enzymes catalyze the steps necessary for carrying out the steps of optionally aromatic amino acid production, BH4 production, and oxidation product production. If an intermediate has been introduced, the expressed enzymes catalyze those steps necessary to convert the intermediate into the respective oxidation product. Any means for recovering the oxidation product from the host cell may be used. For example, the host cell may be harvested and subjected to hypotonic conditions, thereby lysing the cells. The lysate may then be centrifuged and the supernatant subjected to high performance liquid chromatography (HPLC) or gas chromatography (GC). Once the oxidation product is recovered, modification, as desired, may be carried out on the oxidation product.

Host Cells

The host cells of the present invention are genetically modified in that heterologous nucleic acid have been introduced into the host cells, and as such the genetically modified host cells do not occur in nature. The suitable host cell is one capable of expressing a nucleic acid construct encoding one or more enzymes described herein involved in the oxidation of an aromatic amino acid, and/or in the regeneration of BH4. The gene(s) encoding the enzyme(s) may be heterologous to the host cell or the gene may be native to the host cell but is operatively linked to a heterologous promoter and one or more control regions which result in a higher expression of the gene in the host cell.

The enzyme can be native or heterologous to the host cell. Where the enzyme is native to the host cell, the host cell is genetically modified to modulate expression of the enzyme. This modification can involve the modification of the chromosomal gene encoding the enzyme in the host cell or a nucleic acid construct encoding the gene of the enzyme is introduced into the host cell. One of the effects of the modification is the expression of the enzyme is modulated in the host cell, such as the increased expression of the enzyme in the host cell as compared to the expression of the enzyme in an unmodified host cell.

In some embodiments, the host cell natively comprises a nucleic acid encoding an enzyme capable of phenylacetaldehyde dehydrogenase into 3,4-dihydroxyphenyl acetate (3,4-DHPA), such as the enzyme phenylacetaldehyde dehydrogenase, wherein the host cell is reduced in the expression of the enzyme. When the host cell is *E. coli*, the enzyme is phenylacetaldehyde dehydrogenase encoded by the feaB gene. The reduced expression can be the result of a mutation that reduced expression or reduces enzymatic activity of the enzyme. An example of such a mutation is a truncated or deleted gene, such as a knock out mutation.

Any prokaryotic or eukaryotic host cell may be used in the present method so long as it remains viable after being transformed with a sequence of nucleic acids. Generally, although not necessarily, the host microorganism is bacterial. Examples of bacterial host cells include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla,* and *Paracoccus* taxonomical classes. Preferably, the host cell is not adversely affected by the transduction of the necessary nucleic acid sequences, the subsequent expression of the proteins (i.e., enzymes), or the resulting intermediates required for carrying out the steps associated with the mevalonate pathway. For example, it is preferred that minimal "cross-talk" (i.e., interference) occur between the host cell's own metabolic processes and those processes involved with the mevalonate pathway. Suitable eukaryotic cells include, but are not limited to, fungal, insect or mammalian cells. Suitable fungal cells are yeast cells, such as yeast cells of the *Saccharomyces* genus.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

Oxidation of L-Tyrosine

Figure 10:
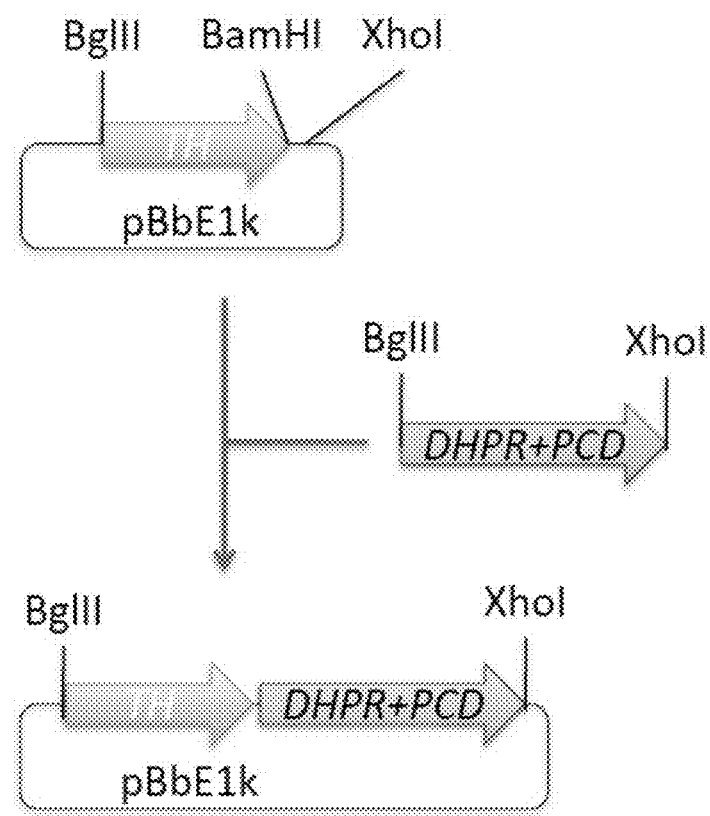
FIG. 10 shows the construction of vector pBbE1k. Plasmid is constructed with TH and without or with BH4 regen.

To reconstitute L-tyrosine hydroxylation in *E. coli* using tyrosine hydroxylase, three components are used: tyrosine hydroxylase, BH4 biosynthetic pathway, and BH4 regeneration pathway. First, TH from mouse is employed for L-DOPA production. *E. coli* codon optimized mouse TH is synthesized and cloned into pBbE1k vector using BglBrick standard cloning (see FIG. 10). TH expression is confirmed by SDS-PAGE (data not shown) and the activity of TH is judged by the color change of the culture supplemented with L-tyrosine since the oxidation product L-DOPA easily forms black pigment (melanin) in aerobic culture. However the *E. coli* harboring pBbE1k-TH did not show the significant the color change of the culture, even though TH is expressed as a soluble form. This result is expected since the cofactor BH4 and its regeneration pathway are not present in *E. coli*, and even the active enzyme cannot oxidize L-tyrosine unless the active cofactor is present. The BH4 regeneration pathway (FIG. 4A) and BH4 biosynthetic pathway in *E. coli*. (FIG. 9) are constructed. To build BH4 regeneration pathway, pterin-4 alpha-carbinolamine dehydratase (PCD) and dihydropteridine reductase (DHPR) are synthesized and incorporated them into pBbE1k vector using BglBrick standard cloning. The resulting plasmid (pBbE1k-Regen) is expressed in *E. coli* BLR strain and protein overexpression is confirmed by SDS-PAGE (data not shown). BH4 biosynthesis involves two additional genes; the 6-pyruvoyl-tetrahydropterin synthase (PTPS-II) which catalyzes the conversion of 7,8-dihydroneopterin triphosphate ($H_2$-NPt-P3) to 6-pyruvoyl-tetrahydropterin (P-$H_4$-Pt) and sepiapterin reductase (SR) which is an oxidoreductase required for the final two-step reduction of the diketo intermediate P-$H_4$-Pt to BH4 (FIG. 9). The biosynthesis of BH4 in *E. coli* has been reported previously. Current efforts to clone these two genes in *E. coli* expression vector have not been successful. This may be due to the toxic effect of these gene products in *E. coli*.

A plasmid is constructed with both TH and BH4 regeneration pathway together in pBbE1k vector to test the activity of TH and BH4 regeneration pathway in vitro. The resulting plasmid (pBbE1k-TH-Regen) is transformed into *E. coli* BLR strain, and the proteins are expressed for 6 hours post induction. The cell lysate is prepared and used for in vitro activity test of TH and BH4 regeneration pathway with supplementing BH4 and L-tyrosine as substrates.

Figure 14:
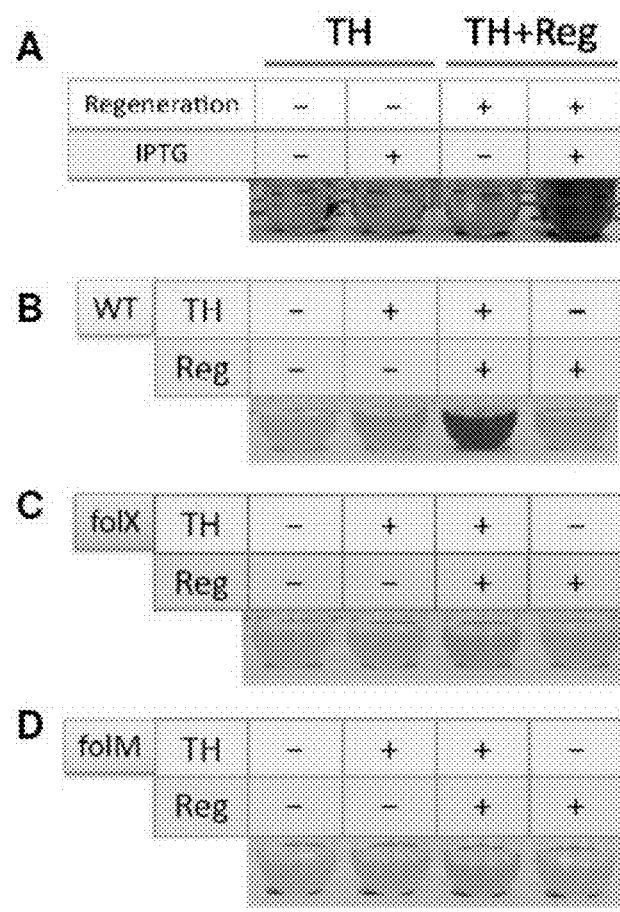
FIG. 14 shows the experimental results from Example 1 showing whether melanin is produced in each culture.
Figure 15:
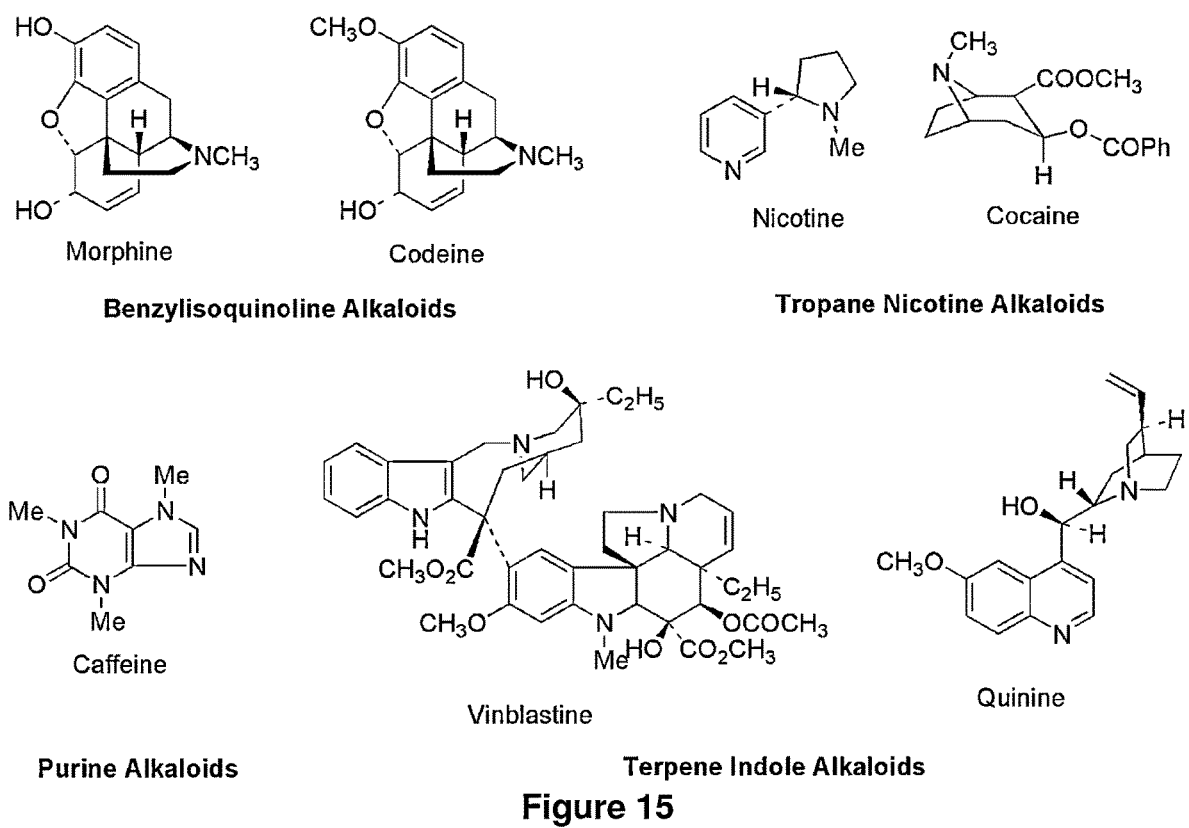
FIG. 15 shows the structures of various alkaloids, including benzyl isoquinoline alkaloids (BIA).
Figure 16:
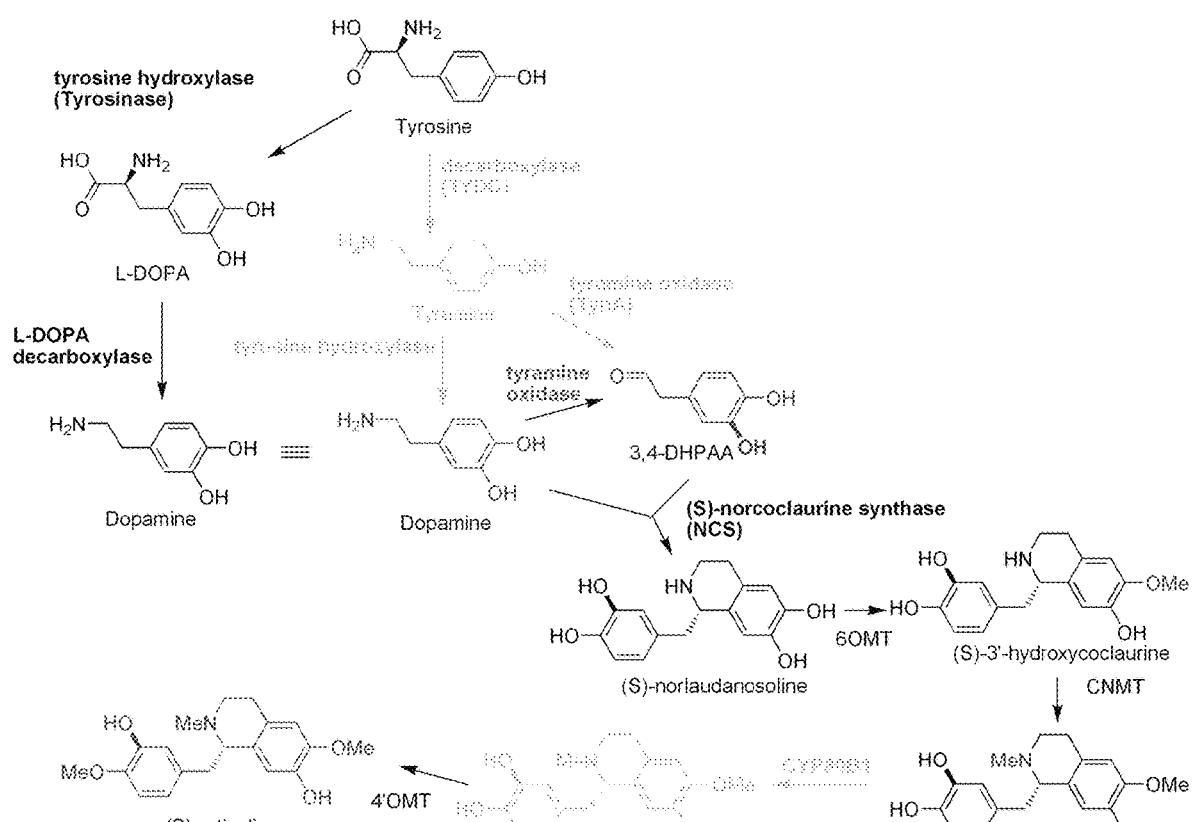
FIG. 16 shows a biosynthetic pathway to synthesize reticuline from dopamine, and from tyrosine.
Figure 17:
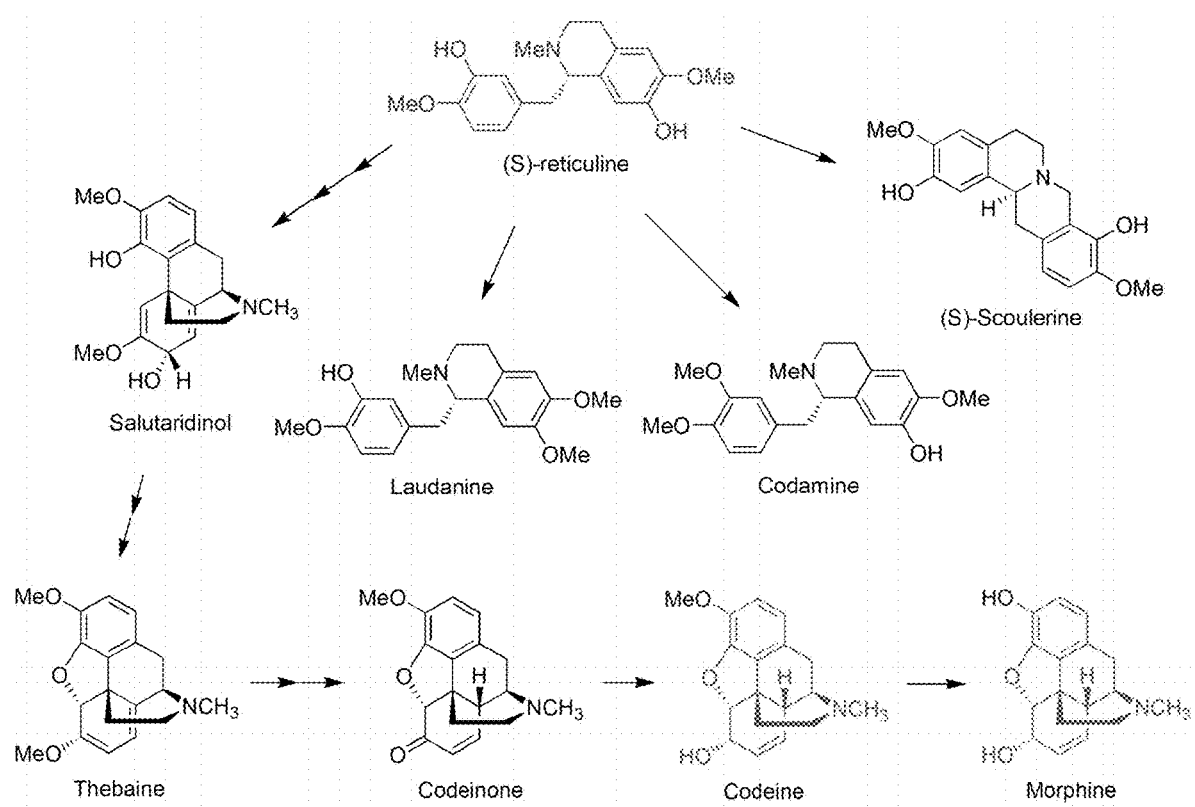
FIG. 17 shows a biosynthetic pathway to synthesize BIA, among other compounds, from reticuline.

The attempt to test L-DOPA production in vivo has followed with and without adding BH4 in the growth media containing L-tyrosine, and interestingly the color change is observed in the control without BH4 supplementation when both TH and BH4 regeneration pathway are present (FIG. 14A). The control strain that does not express TH did not show any color change as expected, and the strain that expresses only TH without BH4 regeneration pathway did not show color change either regardless the presence of BH4 cofactor. This observation suggests that there may be an alternative endogenous cofactor in *E. coli* that can take the role of BH4 in the tyrosine oxidation by TH.

Tetrahydromonapterin (MH4 or H4-MPt) is a major pterin in *E. coli* and has been proposed as the cofactor for phenylalanine hydroxylase (PAH). Based on the functional and structural similarity of PAH and TH enzymes, MH4 is hypothesized that it can be used as the alternative cofactor to BH4 in tyrosine hydroxylation by TH. To confirm this hypothesis, an in vivo L-DOPA production experiment is performed by expressing TH and BH4 regeneration pathway in the mutant strain which cannot synthesize MH4. It has been reported that FolM and FolX is related to MH4 biosynthesis as shown in FIG. 9. Single gene knockout mutants of folM and folX from Keio knockout collection with the *E. coli* strain BW25113 background is obtained and the tyrosine hydroxylase and BH4 regeneration pathway genes are introduced into them. As shown in FIG. 14B-D, the cultures of these mutants expressing pBbE1k-TH-Regen did not turn into black under the same condition that oxidized L-tyrosine to L-DOPA as described above. On the other hand, the wild type strain changed the color in the same condition as previously observed. This demonstrates that MH4 is used as the alternative to BH4 in tyrosine hydroxylation by TH in *E. coli*.

Even though the new pathway to oxidize L-tyrosine to L-DOPA by TH in *E. coli* is demonstrated, the actual production of L-DOPA is not quantified since L-DOPA is easily oxidized to o-quinone and further to black pigment such as melanin very quickly unless reducing agent such as ascorbic acid is used in the producing media.

Figure 5:
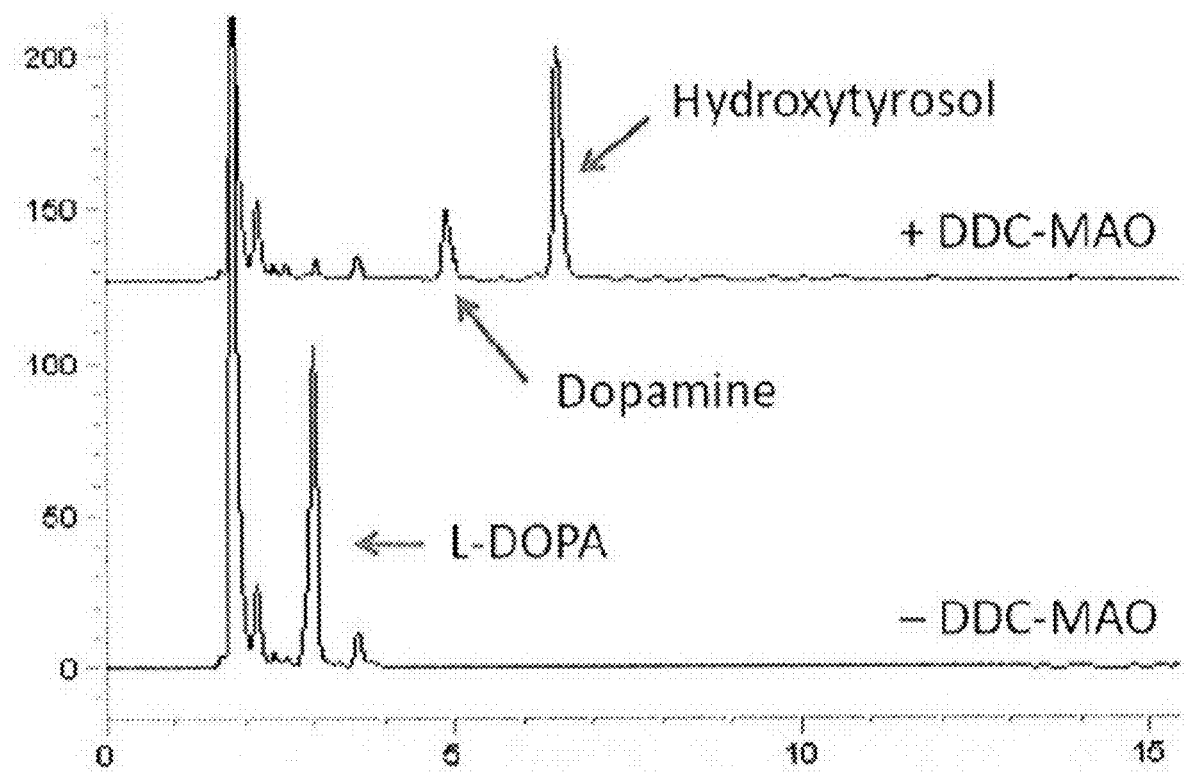
FIG. 5 shows hydroxytyrosol production from L-DOPA.

In the above sections, L-DOPA formed is detected as melanin. It is expected that hydroxytyrosol (3,4-hydroxyphenetylethanol) can be synthesized from L-DOPA in the same manner (FIG. 5). However, tyramine oxidase (TDC) from *P. somuniferum* used for the tyrosol production is not suitable for hydroxytyrosol production, because TDC reacts with tyrosine, precursor for L-DOPA. Based on a survey, L-DOPA decarboxylase (DDC) from pig is employed in this experiment instead of TDC. The DDC gene is inserted at upper region of TYO from *M. luteus* in pBbS1a-1, and resultant plasmid is designated pBbS1a-3.

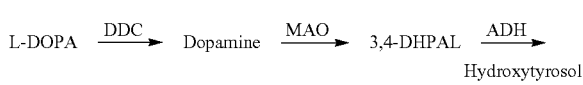

TABLE 1

| | Hydroxytyrosol [mM] |
|---|---|
| DDC-MAO | 0.74 |
| Control | 0 |

Figure 6:
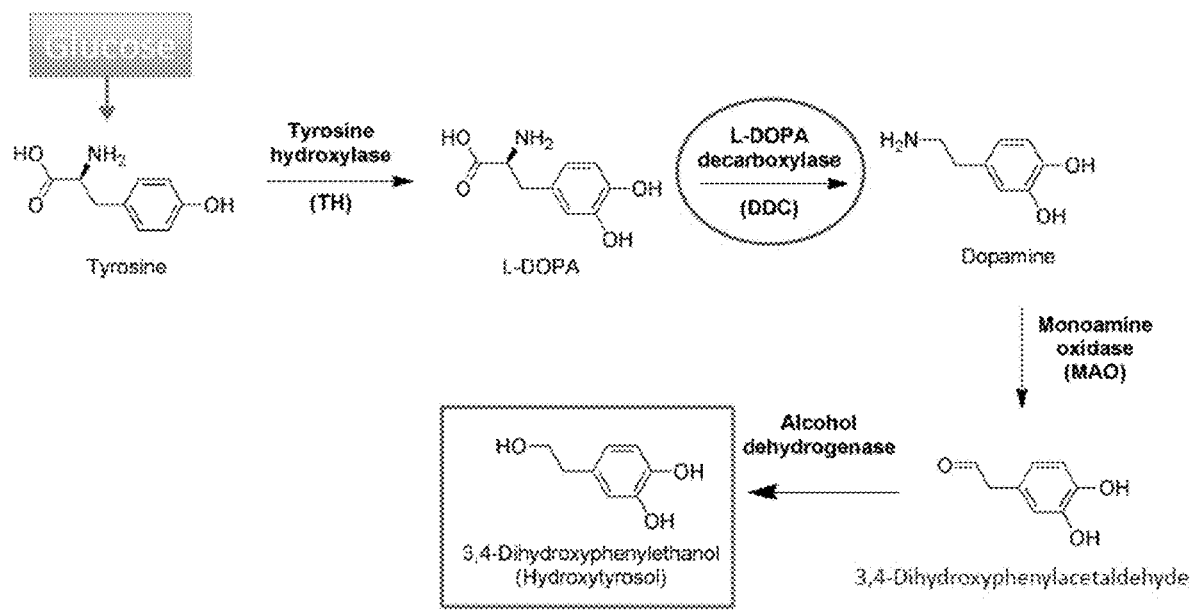
FIG. 6 shows hydroxytyrosol production from tyrosine. "TH" is tyrosine hydroxylase (which can be synthesized from mouse), "DDC" is L-DOPA decarboxylase (which can be synthesized from pig, "MAO" is monoamine oxidase (which can be cloned from *Micrococcus luteus*.

The strains harboring pBbE1k and pBbS1a derivatives are cultured in M9 medium supplemented with yeast extract. The color of the culture of E. coli harboring pBbE1k-3 and pBbS1a-3 is not changed back, while the color of the culture of E. coli harboring pBbE1k-3 and pBbS1a is changed. As shown in FIG. 6, the strain harboring both pBbE1k-3 and pBbS1a-3 was successfully produced 0.08 mM of hydroxytyrosol.

TABLE 2

| pBbE1k | P8bS1a | Tyrosine | Hydroxytyrosol [mM] |
|---|---|---|---|
| TH-Reg | DDC-MAO | + | 0.19 |
| TH-Reg | DDC-MAO | − | 0.06 |
| Control | DDC-MAO | + | 0 |
| Control | DDC-MAO | − | 0 |

For the oxidation of L-tyrosine, tyrosine hydroxylase (TH), which hydroxylates tyrosine to L-DOPA using tetrahydrobiopterin (BH4) as a cofactor, is employed.

Although it has been known that E. coli does not produce BH4, TH is found to be able to function and synthesizes L-DOPA from the central metabolic tyrosine in cells co-expressing pterin-4 alpha-carbinolamine dehydratase (PCD) and dihydropteridine reductase (DHPR) for BH4 regeneration. Tetrahydromonapterin (MH4) is an alternative for BH4 by using the MH4-production mutants. Furthermore, in order to elucidate the availability of the E. coli for L-DOPA derivatives, it is combined with the pathway for aryl alcohol production pathway. As a result, the strain successfully produces hydroxytyrosol, a powerful antioxidant.

MH4, which is produced by E. coli and secreted into the media, can function as an alternative of BH4. Furthermore the BH4 regeneration pathway in human is effectively regenerated MH4 from MH2 formed during the hydroxylation reaction of TH. The data indicates that all enzymes, TH, PCD and DHPR are able to recognize not only BH4 but also MH4.

It is known that TH, which catalyzes the conversion of tyrosine to L-DOPA with $H_2O$ and BH4 as a substrate and a cofactor, respectively (FIG. 4A), is an important enzyme related to the synthesis of neurotransmitters such as adrenalin, noradrenalin, and dopamine in animals. Although this enzyme is a potent candidate for metabolic engineering to produce L-DOPA, there is no report about its application. One of the reasons is limited availability of the coenzyme BH4. It has been known that BH4 is a unique cofactor for animal and no bacterium used in general for industrial fermentation processes accumulates it. Recently, it has been reported that pterin-dependent enzyme phenylalanine hydroxylase (PAH) related to tyrosine formation from phenylalanine from Pseudomonas aeruginosa can compliment tyrosine auxotrophy of E. coli and used MH4 as cofactors. Homology search of PAH and TH indicate a high degree of sequence identity/similarity. These data encouraged us to apply TH to L-DOPA synthesis because the structure of BH4 and MH4 is almost same. The difference is merely the structure of the side-chains.

Figure 4:
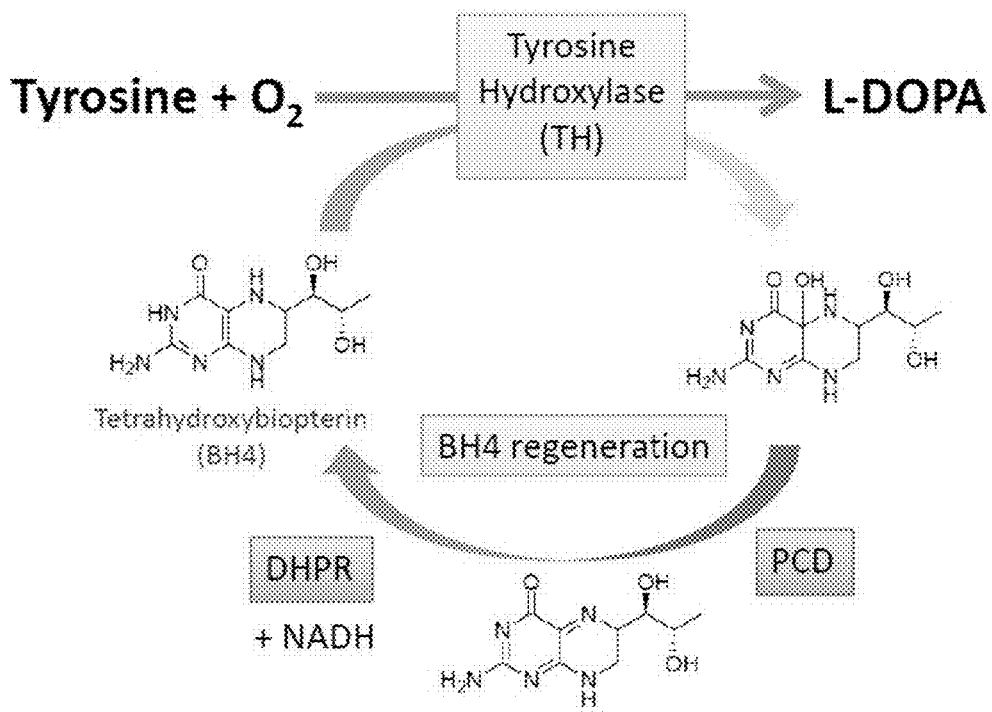
FIG. 4 shows (A) tyrosine oxidation by tyrosine hydroxylase and the Pterin cofactor regeneration pathway, and (B) tryptophan oxidation by tryptophan hydroxylase and the Pterin cofactor regeneration pathway.
Figure 4:
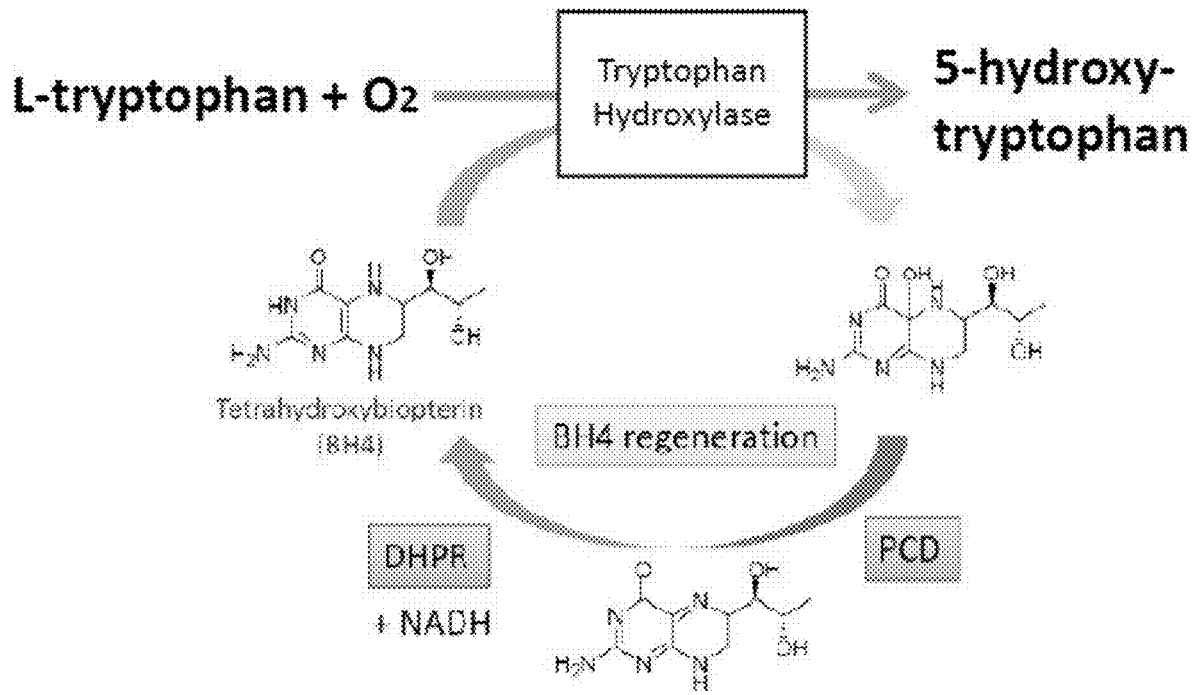

L-DOPA Production from Glucose. E. coli BLR(DE3) and tyrosine-overproducing strain derived it are tested in M9 medium. The level of L-DOPA production is determined on the basis of melanin formation measuring absorbance at 400 nm. The data is shown in FIG. 4. Both of the strains including pBbE1k-3 indicated higher absorption than the controls, demonstrating they were able to convert tyrosine supplied via the central metabolic pathway into L-DOPA. In addition, the tyrosine-overproducing strains show much higher melanin formation. In conclusion, an E. coli construct capable of producing L-DOPA producing from renewable carbon source is produced.

Figure 7:
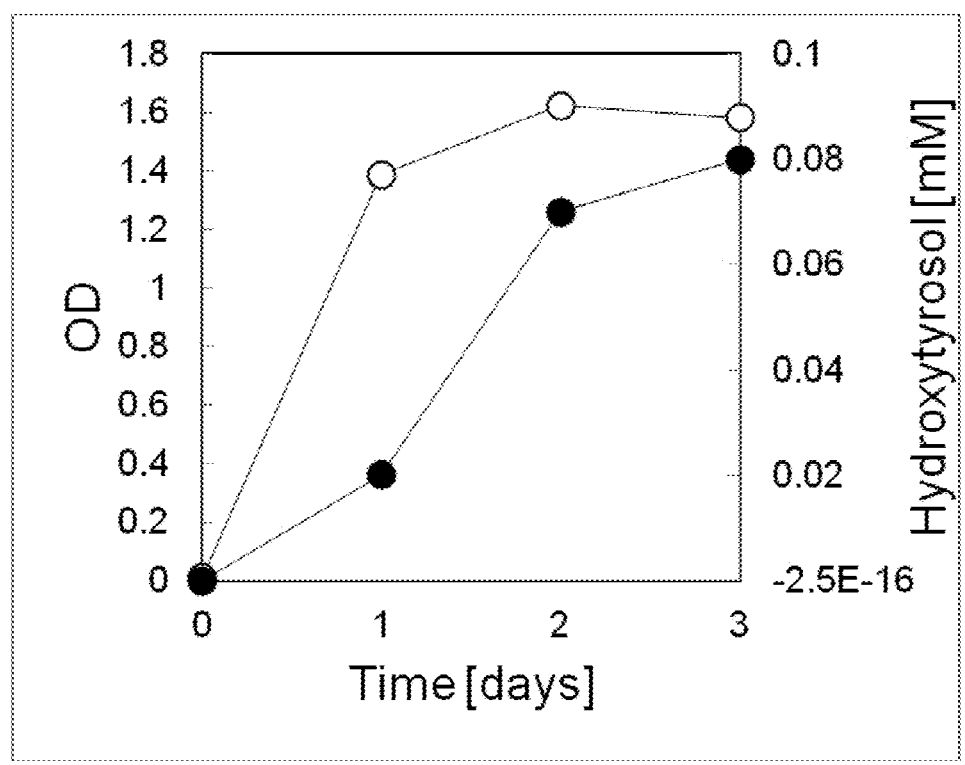
FIG. 7 shows hydroxytyrosol biosynthesis from glucose (with native level of tyrosine). The open circles indicate the OD. The closed circles indicate the concentration of hydroxytyrosol.

E. coli feaB mutant harboring pBbS 1a-DDC-MAO and pBbE1k-TH-Reg. An overnight culture of the strain is used to inoculate 2 mL of fresh LB media which is cultured for 4 hours at 30° C. The cells are then harvested and washed, and used to inoculate 50 mL of M9Y media and are cultured for 3 hours at 30° C. IPTG is then added to give a final concentration of 0.5 mM. The sample is analyzed every day. See FIG. 7.

Discussion

For animals, plants, fungus, and bacteria, L-DOPA is an important compound. For example, L-DOPA is a precursor for neurotransmitters such as adrenalin, noradrenalin, and dopamine. In addition, certain plants derive their derivatives such as pharmaceutical alkaloids, morphine, codeine, and tebaine and so on. L-DOPA is currently manufactured employing petroleum as the raw material. Concerns about the non-renewable nature of petroleum as well as the pollution generated from the manufacturing processes have been a driving force to develop alternate sustainable production methods.

In animal brains, L-DOPA is synthesized from tyrosine by using TH. However, the application of the enzyme to metabolic engineering has not yet been reported. One of the issues would be availability of the coenzyme BH4. BH4 is a unique cofactor for animal and no bacterium used in general for industrial fermentation processes biosynthesize it. Here it is reported that MH4, which is produced by E. coli and secreted into the media, can function as an alternative of BH4. Furthermore BH4 regeneration pathway in human effectively regenerated MH4 from MH2 formed during the hydroxylation reaction of TH. These data indicate that all enzymes, TH, PCD and DHPR are able to recognize not only BH4 but also MH4.

Materials and Methods

Bacterial Strains and Cultures. Escherichia coli DH10B (Life Technologies, Grand Island, N.Y.) is routinely used for plasmid construction. In addition, E. coli BL21 BLR and its tyrosine-overproducing strain A200, and E. coli BW25113 and its feaB, folM, folX knockout mutant JW1380, JW1598, and JW2300, respectively, in the Keio collection (Baba, T., et al., Construction of Escherichia coli K-12 in-frame, single-gene knockout mutants: the Keio collection. Mol Syst Biol, 2006. 2: p. 2006; hereby incorporated by reference) are employed for L-DOPA production and hydroxytyrosol production, respectively. The strain JW1380 is used after eliminating kanamycin resistance gene in the chromosome as described by Datsenko and Wanner (Datsenko, K. A. and B. L. Wanner, One-step inactivation of chromosomal genes in Escherichia coli K-12 using PCR products. Proc Natl Acad Sci USA, 2000. 97(12): p. 6640; hereby incorporated by reference).

The medium used are LB broth medium (Lennox; BD, NJ) and M9 minimal medium (M9 minimal salts (BD, NJ), 1% (w/v) glucose, 5 mM $MgSO_4$, 0.1 mM $CaCl_2$). When needed, kanamycin and carbenicillin are added to the medium at 50 and 100 μg/mL, respectively.

Plasmids Construction. In order to enable rapid cloning and assembly of genes, BglBrick cloning strategy is employed. Tyrosine hydroxylase gene from mouse (TH, accession no. NP_033403), PCD gene from human (PCD, accession no. NP_000272), L-DOPA decarboxylase gene from pig (DDC) and other suitable genes with a ribosome binding site, which are optimized to codon usage for E. coli by using Gene Designer 2.0 software (DNA 2.0 Inc., Menlo Park, Calif.), purchased from GeneScript (NJ). BglBrick compatible vectors pBbE1k (ColE1 ori, trc promoter, lacI$^q$, Km$^r$) and pBbS1a (SC101 ori, trc promoter, lacI$^q$, Ap$^r$) are used in order to construct appropriate plasmids including artificial operons based on BglBrick strategy (Anderson et al.: BglBricks: A flexible standard for biological part assembly. Journal of Biological Engineering 2010 4:1; http://openwetware.org/wiki/BBb; hereby incorporated by reference).

HPLC Analysis. Supernatants of cultures (2 µL) are analyzed by an Agilent HPLC system (Agilent Technologies Inc., Santa Clara, Calif.) equipped Discovery HS F5 (15 cm×2.1 mm ID, 3 µm; Sigma-Aldrich, MO). BufferA (0.1% formic acid solution) and bufferB (acetonitrile with 0.1% formic acid) are used as a mobile phase and compounds are eluted at 35° C. and 0.3 mL/min of flow rate with increasing concentrations of bufferB as follows: 5%, 0-2 min; 5-30%, 2-22 min. Eluted compounds are detected by a diode array spectrophotometer measuring an absorbance at 280 nm or a mass spectrometer. Tyrosine, L-DOPA, dopamine, tyramine, tyrosol, and 3,4-dihydroxyphenylacetate (DHPA) (Sigma-Aldrich), hydroxytyrosol are used as standards.

L-DOPA Production. *E. coli* harboring pBbE1k derivatives are cultured in LB medium for 16 hr at 37° C. The aliquots (1 mL or 0.1 mL) are inoculated into 250 mL shake flasks containing 50 mL or test tubes containing 5 mL of LB medium, respectively. These are cultured at 30° C. for 3 hr and then isopropyl β-D-thiogalactopyranoside (IPTG) is added at the concentration of 0.5 mM and the cells are cultured for addition 20 hr at 30° C. The supernatants of shake flask cultures are collected in test tubes to be photographed.

Hydroxytyrosol Production. Shake flask experiments are performed in 250 mL Erlenmeyer flasks containing 50 mL of M9Y medium. The aliquots (50 µL) of overnight culture is inoculated into fresh 2 mL LB medium and cultured at 30° C. for 4 hr. Then the cells are harvested and washed once with same amount of M9Y medium. The all cells are inoculated into 50 mL of M9Y medium. They are cultured for 3 hr at 30° C., 160 rpm and IPTG is added at final concentration of 0.5 mM. Samples (1 mL) collected at appropriate time points are analyzed by HPLC. Optical density (OD) measurements at 600 nm are also taken using a Beckman spectrophotometer.

HPLC Analysis. Supernatants of cultures (2 µL) are analyzed by an Agilent HPLC system equipped Discovery HS F5 (15 cm×2.1 mm ID, 3 µm; Sigma-Aldrich, MO). BufferA (0.1% formic acid solution) and bufferB (acetonitrile with 0.1% formic acid) are used as a mobile phase and compounds are eluted at 35° C. and 0.3 mL/min of flow rate with increasing concentrations of bufferB as follows: 5%, 0-2 min; 5-30%, 2-22 min. Eluted compounds are detected by a diode array spectrophotometer measuring an absorbance at 280 nm or a mass spectrometer. Tyrosine, tyramine, tyrosol, and 4-hydroxyphenylacetate (4HPA) (Sigma-Aldrich) are used as standards.

EXAMPLE 2

Producing Hydroxytyrosol Using Host Cell Containing DDC

Figure 11:
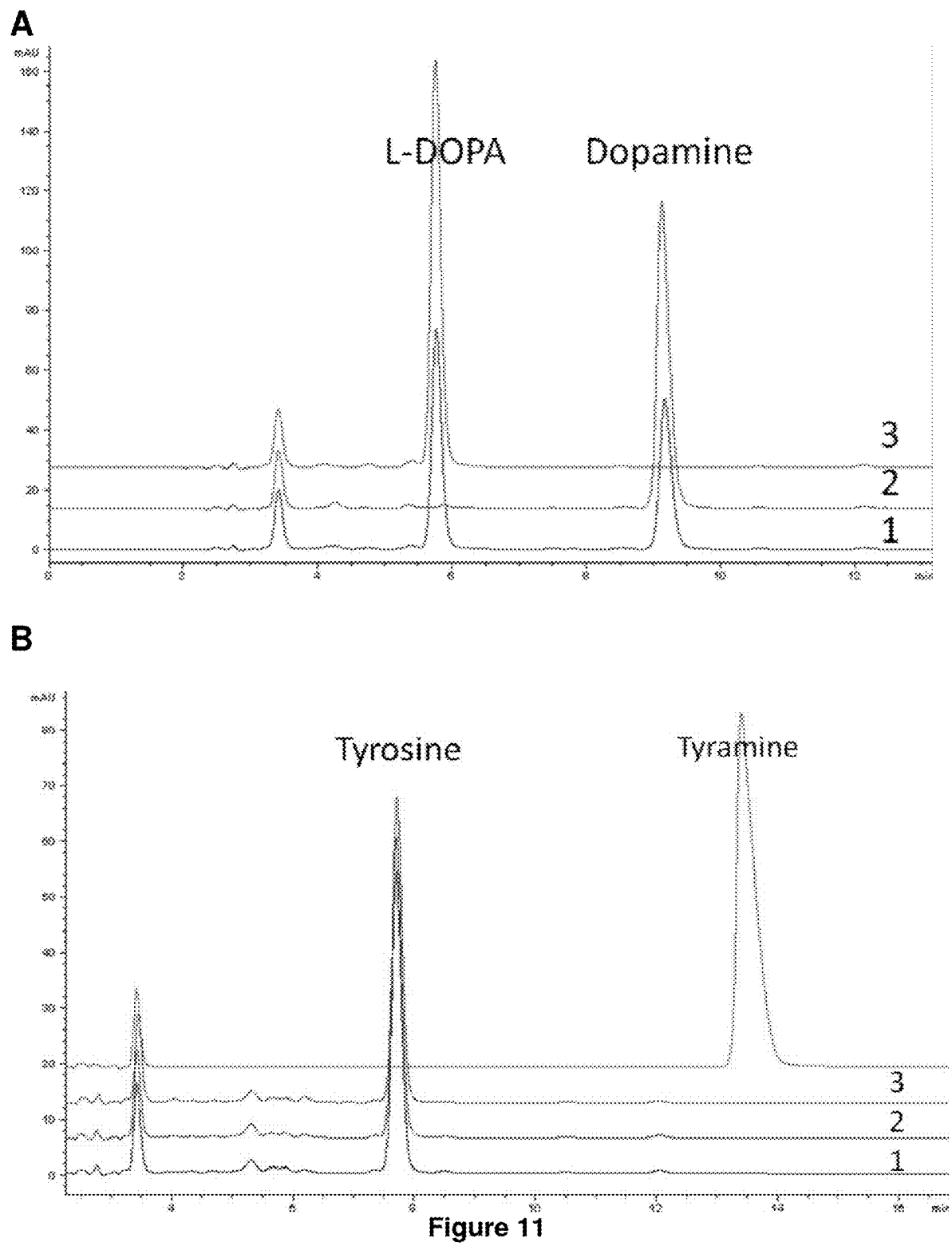
FIG. 11 shows hydroxytyrosol production from tyrosine using DDC. For both Panels A and B: sample 1 is BLR/pBbE1k-DDC1, induced; sample 2 is BLR/pBbE1k-DDC1, uninduced; sample 3 is BLR/pBbE1k, induced (control).

It is useful to have a gatekeeper to prevent the production of tyrosol (which is a much less potent antioxidant compared to hydroxytyrosol) when producing hydroxytyrosol from tyrosine. In the biosynthetic scheme shown in FIG. 2, the pathway does not include any such gatekeeping process and it is hard to avoid the formation of tyrosol. In the biosynthetic scheme tested in Example 2, aromatic acid oxidation is the first step of the pathway and this is the first step to differentiate hydroxytyrosol pathway from tyrosol pathway. The next step is the decarboxylation of L-DOPA, and this is chosen as a gatekeeping step. A suitable L-DOPA specific decarboxylase is one from pig. The activity of this enzyme is tested toward both L-DOPA and L-tyrosine and it is confirmed that it is only active toward L-DOPA for decarboxylase function, and has extremely weak or no activity for converting L-tyrosine into tyramine. See FIG. 11.

EXAMPLE 3

Producing Hydroxytyrosol Using Host Cell Containing a feaB Knock Out Mutation

The production of hydroxytyrosol from dopamine is tested by overexpressing monoamine oxidase from *Micrococcus luteus* which converts dopamine into 3,4-dihydroxyphenyl acetaldehyde (3,4-DHPAL). The endogenous alcohol dehydrogenase in *E. coli* can convert this aldehyde to hydroxytyrosol. However, another *E. coli* endogenous enzyme, phenylacetaldehyde dehydrogenase, converts this aldehyde into 3,4-dihydroxyphenyl acetate (3,4-DHPA) and thus lowers both the yield and purity of the hydroxytyrosol produced. An *E. coli* host cell knocked out for feaB gene (which encodes phenylacetaldehyde dehydrogenase; EHX93578.1) is shown to have almost no production of 3,4-DHPA and hydroxytyrosol is the main and almost exclusive product of the strain when the pathway genes are overexpressed. See FIG. 12.

Dopamine →MAO→ DHPAL →ADH→ Hydroxytyrosol

Figure 12:
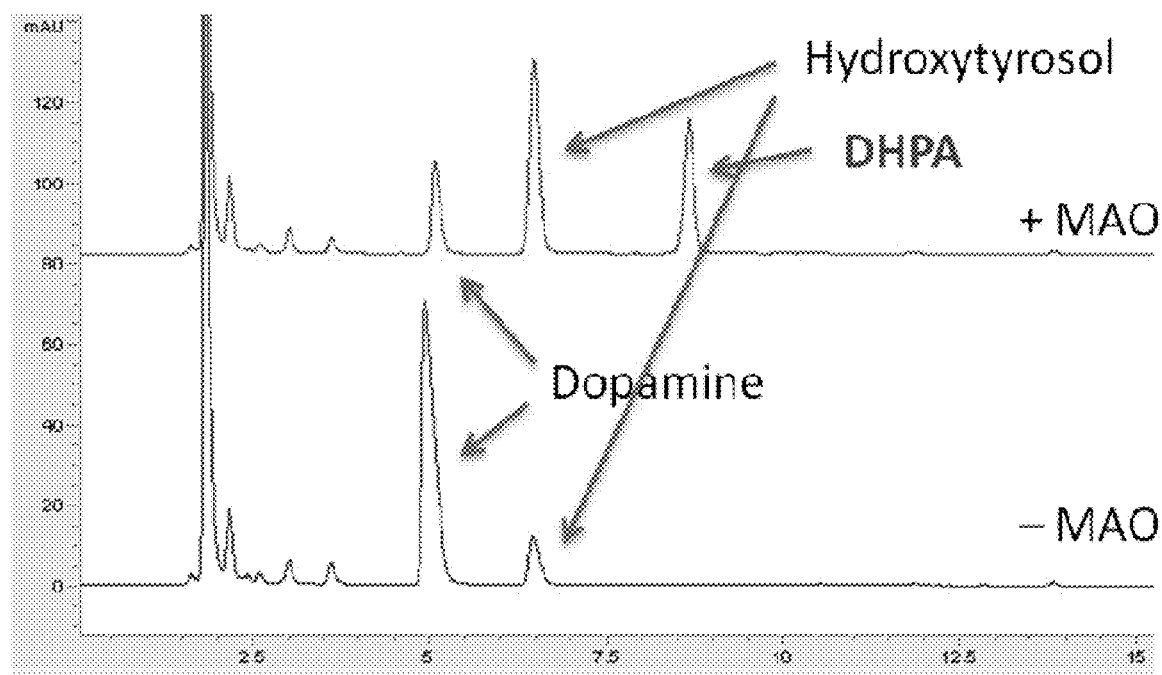
FIG. 12 shows hydroxytyrosol production from dopamine. (A) BW25113 (wild type) harboring pS1a-MAO or pS1a (control), (B) feaB knock out mutant harboring pS1a-MAO or pS1a (control).
Figure 12:
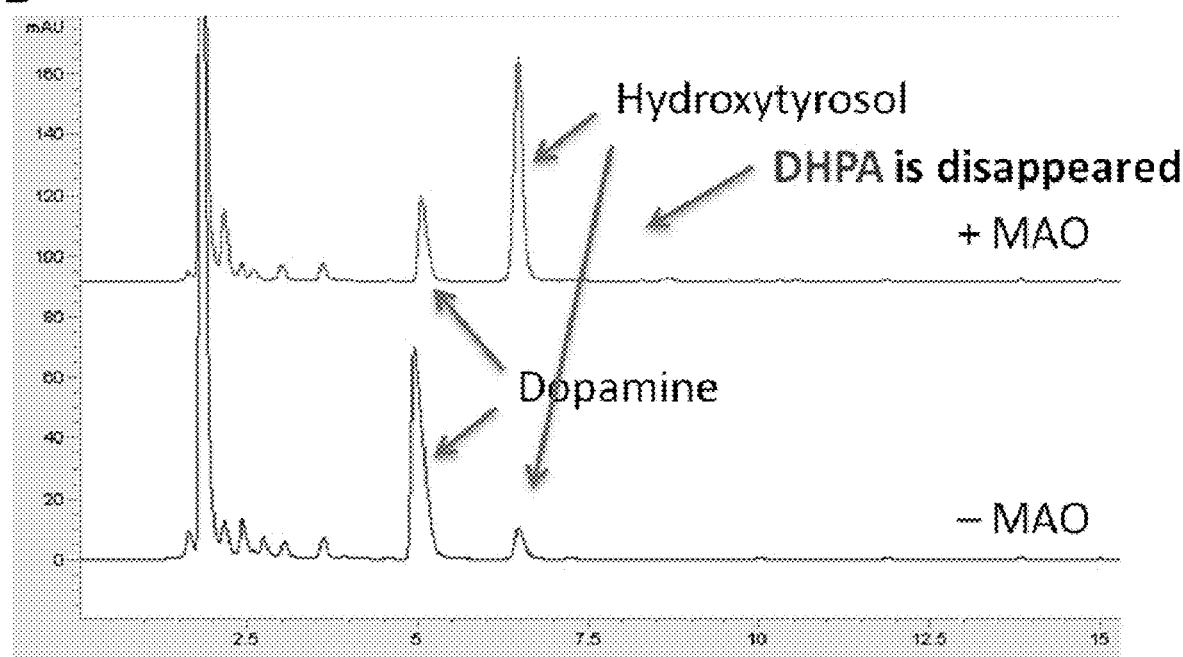

The feaB knockout mutation is a strain modification that achieves high yield and high purity microbial hydroxytyrosol production. FIG. 12, Panel A shows hydroxytyrosol and 3,4-Dihydroxyphenylacetate (DHPA) are produced. *E. coli* has a phenylacetaldehyde dehydrogenase gene (feaB) to produce DHPA. The endogenous *E. coli* MAO may convert Dopamine to the acetaldehyde (DHPAL) for the production of small amount of hydroxytyrosol. See Table 3. FIG. 12, Panel B shows Hydroxytyrosol is a main product. Phenylacetaldehyde dehydrogenase gene (feaB) is closely related to production of DHPA. See Table 4.

TABLE 3

|  | Hydroxytyrosol [mM] | DHPA [mM] |
|---|---|---|
| MAO | 0.47 | 0.31 |
| Control | 0.12 | 0 |

TABLE 4

|  | Hydroxytyrosol [mM] | DHPA [mM] |
|---|---|---|
| MAO | 0.69 | 0 |
| Control | 0.09 | 0 |

EXAMPLE 4

Hydroxytyrosol Biosynthesis from L-DOPA

Figure 13:
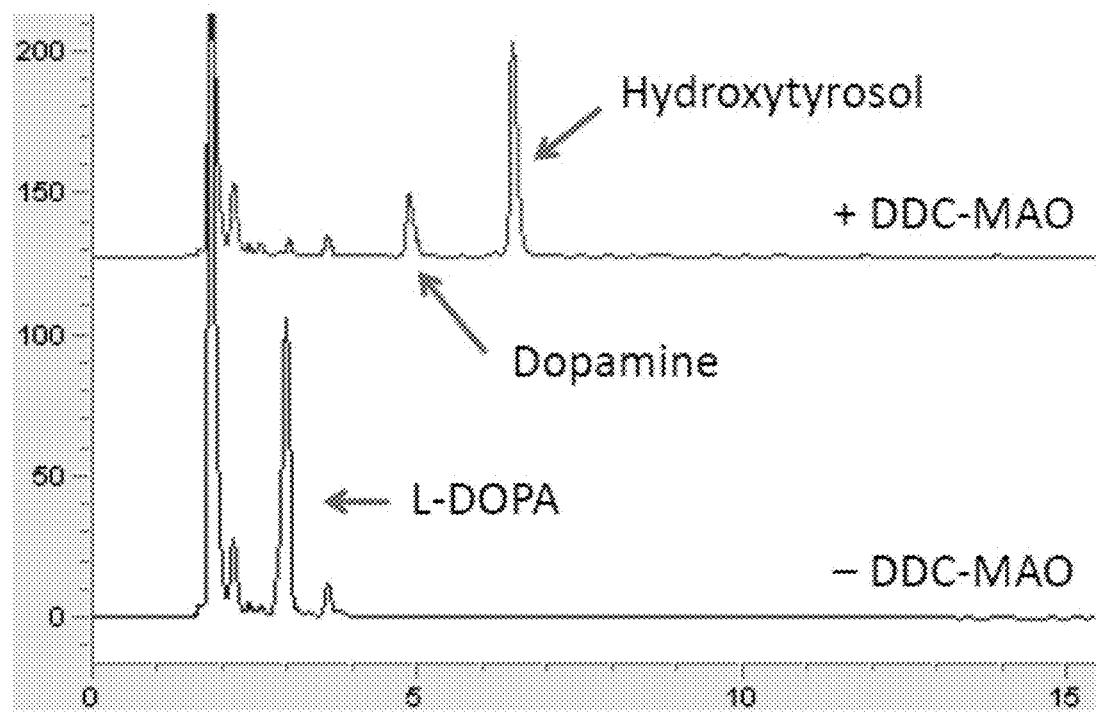
FIG. 13 shows hydroxytyrosol biosynthesis from L-DOPA.

A feaB mutant harboring pS1a-DDC-MAO or pS1a (control) is tested to determine whether hydroxytyrosol is produced. The results indicate MAO is a rate-limiting step under the cultivation condition. See FIG. 13 and Table 5.

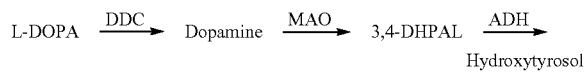

TABLE 5

|         | Hydroxytyrosol [mM] | DHPA [mM] |
|---------|---------------------|-----------|
| DDC-MAO | 0.74                | 0         |
| Control | 0                   | 0         |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A genetically modified host cell capable of producing one or more oxidation products of a tyrosine, comprising or is capable of expressing: (a) a tyrosine hydroxylase (TH), (b) pterin-4-alpha-carbinolamine dehydratase (PCD), and (c) dihydropteridine reductase (DHPR); wherein the host cell is capable of expressing L-DOPA decarboxylase (DDC), monoamine oxidase (MAO), and alcohol dehydrogenase (ADH), and the host cell has a native phenylacetaldehyde dehydrogenase, wherein the phenylacetaldehyde dehydrogenase enzyme is truncated or knocked out.

2. The host cell of claim 1, wherein the TH is mouse TH.

3. The host cell of claim 1, wherein the DDC is pig DDC.

4. The host cell of claim 1, wherein the MAO is *Micrococcus luteus* MAO.

5. The host cell of claim 1, wherein the gene encoding the native phenylacetaldehyde dehydrogenase enzyme is feaB.

\* \* \* \* \*

SEQUENCE LISTING

```
<160> NUMBER OF SEQ ID NOS: 8

<210> SEQ ID NO 1
<211> LENGTH: 498
<212> TYPE: PRT
<213> ORGANISM: Mus musculus

<400> SEQUENCE: 1

Met Pro Thr Pro Ser Ala Ser Ser Pro Gln Pro Lys Gly Phe Arg Arg
1               5                   10                  15

Ala Val Ser Glu Gln Asp Thr Lys Gln Ala Glu Ala Val Thr Ser Pro
                20                  25                  30

Arg Phe Ile Gly Arg Arg Gln Ser Leu Ile Glu Asp Ala Arg Lys Glu
            35                  40                  45

Arg Glu Ala Ala Ala Ala Ala Ala Ala Val Ala Ser Ala Glu
    50                  55                  60

Pro Gly Asn Pro Leu Glu Ala Val Val Phe Glu Glu Arg Asp Gly Asn
65                  70                  75                  80

Ala Val Leu Asn Leu Leu Phe Ser Leu Arg Gly Thr Lys Pro Ser Ser
                85                  90                  95

Leu Ser Arg Ala Leu Lys Val Phe Glu Thr Phe Glu Ala Lys Ile His
            100                 105                 110

His Leu Glu Thr Arg Pro Ala Gln Arg Pro Leu Ala Gly Ser Pro His
        115                 120                 125

Leu Glu Tyr Phe Val Arg Phe Glu Val Pro Ser Gly Asp Leu Ala Ala
    130                 135                 140

Leu Leu Ser Ser Val Arg Arg Val Ser Asp Asp Val Arg Ser Ala Arg
145                 150                 155                 160

Glu Asp Lys Val Pro Trp Phe Pro Arg Lys Val Ser Glu Leu Asp Lys
                165                 170                 175

Cys His His Leu Val Thr Lys Phe Asp Pro Asp Leu Asp Leu Asp His
            180                 185                 190

Pro Gly Phe Ser Asp Gln Ala Tyr Arg Gln Arg Arg Lys Leu Ile Ala
        195                 200                 205

Glu Ile Ala Phe Gln Tyr Lys Gln Gly Glu Pro Ile Pro His Val Glu
    210                 215                 220

Tyr Thr Lys Glu Glu Ile Ala Thr Trp Lys Glu Val Tyr Ala Thr Leu
225                 230                 235                 240

Lys Gly Leu Tyr Ala Thr His Ala Cys Arg Glu His Leu Glu Ala Phe
                245                 250                 255
```

-continued

```
Gln Leu Leu Glu Arg Tyr Cys Gly Tyr Arg Glu Asp Ser Ile Pro Gln
        260                 265                 270

Leu Glu Asp Val Ser His Phe Leu Lys Glu Arg Thr Gly Phe Gln Leu
        275                 280                 285

Arg Pro Val Ala Gly Leu Leu Ser Ala Arg Asp Phe Leu Ala Ser Leu
    290                 295                 300

Ala Phe Arg Val Phe Gln Cys Thr Gln Tyr Ile Arg His Ala Ser Ser
305                 310                 315                 320

Pro Met His Ser Pro Glu Pro Asp Cys Cys His Glu Leu Leu Gly His
                325                 330                 335

Val Pro Met Leu Ala Asp Arg Thr Phe Ala Gln Phe Ser Gln Asp Ile
            340                 345                 350

Gly Leu Ala Ser Leu Gly Ala Ser Asp Glu Glu Ile Glu Lys Leu Ser
        355                 360                 365

Thr Val Tyr Trp Phe Thr Val Glu Phe Gly Leu Cys Lys Gln Asn Gly
    370                 375                 380

Glu Leu Lys Ala Tyr Gly Ala Gly Leu Leu Ser Ser Tyr Gly Glu Leu
385                 390                 395                 400

Leu His Ser Leu Ser Glu Glu Pro Glu Val Arg Ala Phe Asp Pro Asp
                405                 410                 415

Thr Ala Ala Val Gln Pro Tyr Gln Asp Gln Thr Tyr Gln Pro Val Tyr
            420                 425                 430

Phe Val Ser Glu Ser Phe Ser Asp Ala Lys Asp Lys Leu Arg Asn Tyr
        435                 440                 445

Ala Ser Arg Ile Gln Arg Pro Phe Ser Val Lys Phe Asp Pro Tyr Thr
    450                 455                 460

Leu Ala Ile Asp Val Leu Asp Ser Pro His Thr Ile Arg Arg Ser Leu
465                 470                 475                 480

Glu Gly Val Gln Asp Glu Leu His Thr Leu Thr Gln Ala Leu Ser Ala
                485                 490                 495

Ile Ser

<210> SEQ ID NO 2
<211> LENGTH: 444
<212> TYPE: PRT
<213> ORGANISM: Homo sapiens

<400> SEQUENCE: 2

Met Ile Glu Asp Asn Lys Glu Asn Lys Asp His Ser Leu Glu Arg Gly
1               5                   10                  15

Arg Ala Ser Leu Ile Phe Ser Leu Lys Asn Glu Val Gly Gly Leu Ile
            20                  25                  30

Lys Ala Leu Lys Ile Phe Gln Glu Lys His Val Asn Leu Leu His Ile
        35                  40                  45

Glu Ser Arg Lys Ser Lys Arg Arg Asn Ser Glu Phe Glu Ile Phe Val
    50                  55                  60

Asp Cys Asp Ile Asn Arg Glu Gln Leu Asn Asp Ile Phe His Leu Leu
65                  70                  75                  80

Lys Ser His Thr Asn Val Leu Ser Val Asn Leu Pro Asn Asp Phe Thr
                85                  90                  95

Leu Lys Glu Asp Gly Met Glu Thr Val Pro Trp Phe Pro Lys Lys Ile
            100                 105                 110

Ser Asp Leu Asp His Cys Ala Asn Arg Val Leu Met Tyr Gly Ser Glu
        115                 120                 125
```

Leu Asp Ala Asp His Pro Gly Phe Lys Asp Asn Val Tyr Arg Lys Arg
            130                 135                 140

Arg Lys Tyr Phe Ala Asp Leu Ala Met Asn Tyr Lys His Gly Asp Pro
145                 150                 155                 160

Ile Pro Lys Val Glu Phe Thr Glu Glu Ile Lys Thr Trp Gly Thr
                165                 170                 175

Val Phe Gln Glu Leu Asn Lys Leu Tyr Pro Thr His Ala Cys Arg Glu
            180                 185                 190

Tyr Leu Lys Asn Leu Pro Leu Leu Ser Lys Tyr Cys Gly Tyr Arg Glu
            195                 200                 205

Asp Asn Ile Pro Gln Leu Glu Asp Val Ser Asn Phe Leu Lys Glu Arg
            210                 215                 220

Thr Gly Phe Ser Ile Arg Pro Val Ala Gly Tyr Leu Ser Pro Arg Asp
225                 230                 235                 240

Phe Leu Ser Gly Leu Ala Phe Arg Val Phe His Cys Thr Gln Tyr Val
            245                 250                 255

Arg His Ser Ser Asp Pro Phe Tyr Thr Pro Glu Pro Asp Thr Cys His
            260                 265                 270

Glu Leu Leu Gly His Val Pro Leu Leu Ala Glu Pro Ser Phe Ala Gln
            275                 280                 285

Phe Ser Gln Glu Ile Gly Leu Ala Ser Leu Gly Ala Ser Glu Glu Ala
            290                 295                 300

Val Gln Lys Leu Ala Thr Cys Tyr Phe Phe Thr Val Glu Phe Gly Leu
305                 310                 315                 320

Cys Lys Gln Asp Gly Gln Leu Arg Val Phe Gly Ala Gly Leu Leu Ser
            325                 330                 335

Ser Ile Ser Glu Leu Lys His Ala Leu Ser Gly His Ala Lys Val Lys
            340                 345                 350

Pro Phe Asp Pro Lys Ile Thr Cys Lys Gln Glu Cys Leu Ile Thr Thr
            355                 360                 365

Phe Gln Asp Val Tyr Phe Val Ser Glu Ser Phe Glu Asp Ala Lys Glu
            370                 375                 380

Lys Met Arg Glu Phe Thr Lys Thr Ile Lys Arg Pro Phe Gly Val Lys
385                 390                 395                 400

Tyr Asn Pro Tyr Thr Arg Ser Ile Gln Ile Leu Lys Asp Thr Lys Ser
            405                 410                 415

Ile Thr Ser Ala Met Asn Glu Leu Gln His Asp Leu Asp Val Val Ser
            420                 425                 430

Asp Ala Leu Ala Lys Val Ser Arg Lys Pro Ser Ile
            435                 440

<210> SEQ ID NO 3
<211> LENGTH: 490
<212> TYPE: PRT
<213> ORGANISM: Homo sapiens

<400> SEQUENCE: 3

Met Gln Pro Ala Met Met Met Phe Ser Ser Lys Tyr Trp Ala Arg Arg
1               5                   10                  15

Gly Phe Ser Leu Asp Ser Ala Val Pro Glu Glu His Gln Leu Leu Gly
            20                  25                  30

Ser Ser Thr Leu Asn Lys Pro Asn Ser Gly Lys Asn Asp Asp Lys Gly
            35                  40                  45

Asn Lys Gly Ser Ser Lys Arg Glu Ala Ala Thr Glu Ser Gly Lys Thr

```
            50              55              60
Ala Val Val Phe Ser Leu Lys Asn Glu Val Gly Gly Leu Val Lys Ala
 65              70              75              80

Leu Arg Leu Phe Gln Glu Lys Arg Val Asn Met Val His Ile Glu Ser
                 85              90              95

Arg Lys Ser Arg Arg Ser Ser Glu Val Glu Ile Phe Val Asp Cys
                100             105             110

Glu Cys Gly Lys Thr Glu Phe Asn Glu Leu Ile Gln Leu Leu Lys Phe
                115             120             125

Gln Thr Thr Ile Val Thr Leu Asn Pro Pro Glu Asn Ile Trp Thr Glu
130             135             140

Glu Glu Glu Leu Glu Asp Val Pro Trp Phe Pro Arg Lys Ile Ser Glu
145             150             155             160

Leu Asp Lys Cys Ser His Arg Val Leu Met Tyr Gly Ser Glu Leu Asp
                165             170             175

Ala Asp His Pro Gly Phe Lys Asp Asn Val Tyr Arg Gln Arg Arg Lys
                180             185             190

Tyr Phe Val Asp Val Ala Met Gly Tyr Lys Tyr Gly Gln Pro Ile Pro
                195             200             205

Arg Val Glu Tyr Thr Glu Glu Thr Lys Thr Trp Gly Val Val Phe
210             215             220

Arg Glu Leu Ser Lys Leu Tyr Pro Thr His Ala Cys Arg Glu Tyr Leu
225             230             235             240

Lys Asn Phe Pro Leu Leu Thr Lys Tyr Cys Gly Tyr Arg Glu Asp Asn
                245             250             255

Val Pro Gln Leu Glu Asp Val Ser Met Phe Leu Lys Glu Arg Ser Gly
                260             265             270

Phe Thr Val Arg Pro Val Ala Gly Tyr Leu Ser Pro Arg Asp Phe Leu
                275             280             285

Ala Gly Leu Ala Tyr Arg Val Phe His Cys Thr Gln Tyr Ile Arg His
                290             295             300

Gly Ser Asp Pro Leu Tyr Thr Pro Glu Pro Asp Thr Cys His Glu Leu
305             310             315             320

Leu Gly His Val Pro Leu Leu Ala Asp Pro Lys Phe Ala Gln Phe Ser
                325             330             335

Gln Glu Ile Gly Leu Ala Ser Leu Gly Ala Ser Asp Glu Asp Val Gln
                340             345             350

Lys Leu Ala Thr Cys Tyr Phe Phe Thr Ile Glu Phe Gly Leu Cys Lys
                355             360             365

Gln Glu Gly Gln Leu Arg Ala Tyr Gly Ala Gly Leu Leu Ser Ser Ile
                370             375             380

Gly Glu Leu Lys His Ala Leu Ser Asp Lys Ala Cys Val Lys Ala Phe
385             390             395             400

Asp Pro Lys Thr Thr Cys Leu Gln Glu Cys Leu Ile Thr Thr Phe Gln
                405             410             415

Glu Ala Tyr Phe Val Ser Glu Ser Phe Glu Glu Ala Lys Glu Lys Met
                420             425             430

Arg Asp Phe Ala Lys Ser Ile Thr Arg Pro Phe Ser Val Tyr Phe Asn
                435             440             445

Pro Tyr Thr Gln Ser Ile Glu Ile Leu Lys Asp Thr Arg Ser Ile Glu
                450             455             460

Asn Val Val Gln Asp Leu Arg Ser Asp Leu Asn Thr Val Cys Asp Ala
465             470             475             480
```

```
Leu Asn Lys Met Asn Gln Tyr Leu Gly Ile
            485                 490

<210> SEQ ID NO 4
<211> LENGTH: 104
<212> TYPE: PRT
<213> ORGANISM: Homo sapiens

<400> SEQUENCE: 4

Met Ala Gly Lys Ala His Arg Leu Ser Ala Glu Glu Arg Asp Gln Leu
1               5                   10                  15

Leu Pro Asn Leu Arg Ala Val Gly Trp Asn Glu Leu Glu Gly Arg Asp
            20                  25                  30

Ala Ile Phe Lys Gln Phe His Phe Lys Asp Phe Asn Arg Ala Phe Gly
        35                  40                  45

Phe Met Thr Arg Val Ala Leu Gln Ala Glu Lys Leu Asp His His Pro
    50                  55                  60

Glu Trp Phe Asn Val Tyr Asn Lys Val His Ile Thr Leu Ser Thr His
65                  70                  75                  80

Glu Cys Ala Gly Leu Ser Glu Arg Asp Ile Asn Leu Ala Ser Phe Ile
                85                  90                  95

Glu Gln Val Ala Val Ser Met Thr
            100

<210> SEQ ID NO 5
<211> LENGTH: 244
<212> TYPE: PRT
<213> ORGANISM: Homo sapiens

<400> SEQUENCE: 5

Met Ala Ala Ala Ala Ala Gly Glu Ala Arg Arg Val Leu Val Tyr
1               5                   10                  15

Gly Gly Arg Gly Ala Leu Gly Ser Arg Cys Val Gln Ala Phe Arg Ala
            20                  25                  30

Arg Asn Trp Trp Val Ala Ser Val Asp Val Val Glu Asn Glu Glu Ala
        35                  40                  45

Ser Ala Ser Ile Ile Val Lys Met Thr Asp Ser Phe Thr Glu Gln Ala
    50                  55                  60

Asp Gln Val Thr Ala Glu Val Gly Lys Leu Leu Gly Glu Glu Lys Val
65                  70                  75                  80

Asp Ala Ile Leu Cys Val Ala Gly Gly Trp Ala Gly Gly Asn Ala Lys
                85                  90                  95

Ser Lys Ser Leu Phe Lys Asn Cys Asp Leu Met Trp Lys Gln Ser Ile
            100                 105                 110

Trp Thr Ser Thr Ile Ser Ser His Leu Ala Thr Lys His Leu Lys Glu
        115                 120                 125

Gly Gly Leu Leu Thr Leu Ala Gly Ala Lys Ala Ala Leu Asp Gly Thr
    130                 135                 140

Pro Gly Met Ile Gly Tyr Gly Met Ala Lys Gly Ala Val His Gln Leu
145                 150                 155                 160

Cys Gln Ser Leu Ala Gly Lys Asn Ser Gly Met Pro Pro Gly Ala Ala
                165                 170                 175

Ala Ile Ala Val Leu Pro Val Thr Leu Asp Thr Pro Met Asn Arg Lys
            180                 185                 190

Ser Met Pro Glu Ala Asp Phe Ser Ser Trp Thr Pro Leu Glu Phe Leu
        195                 200                 205
```

-continued

Val Glu Thr Phe His Asp Trp Ile Thr Gly Lys Asn Arg Pro Ser Ser
    210                 215                 220

Gly Ser Leu Ile Gln Val Val Thr Thr Glu Gly Arg Thr Glu Leu Thr
225                 230                 235                 240

Pro Ala Tyr Phe

<210> SEQ ID NO 6
<211> LENGTH: 486
<212> TYPE: PRT
<213> ORGANISM: Sus scrofa

<400> SEQUENCE: 6

Met Asn Ala Ser Asp Phe Arg Arg Gly Lys Glu Met Val Asp Tyr
1               5                   10                  15

Met Ala Asp Tyr Leu Glu Gly Ile Glu Gly Arg Gln Val Tyr Pro Asp
                20                  25                  30

Val Gln Pro Gly Tyr Leu Arg Pro Leu Ile Pro Ala Thr Ala Pro Gln
            35                  40                  45

Glu Pro Asp Thr Phe Glu Asp Ile Leu Gln Asp Val Glu Lys Ile Ile
    50                  55                  60

Met Pro Gly Val Thr His Trp His Ser Pro Tyr Phe Phe Ala Tyr Phe
65                  70                  75                  80

Pro Thr Ala Ser Ser Tyr Pro Ala Met Leu Ala Asp Met Leu Cys Gly
                85                  90                  95

Ala Ile Gly Cys Ile Gly Phe Ser Trp Ala Ala Ser Pro Ala Cys Thr
            100                 105                 110

Glu Leu Glu Thr Val Met Met Asp Trp Leu Gly Lys Met Leu Gln Leu
    115                 120                 125

Pro Glu Ala Phe Leu Ala Gly Glu Ala Gly Glu Gly Gly Val Ile
130                 135                 140

Gln Gly Ser Ala Ser Glu Ala Thr Leu Val Ala Leu Leu Ala Ala Arg
145                 150                 155                 160

Thr Lys Val Val Arg Arg Leu Gln Ala Ala Ser Pro Gly Leu Thr Gln
                165                 170                 175

Gly Ala Val Leu Glu Lys Leu Val Ala Tyr Ala Ser Asp Gln Ala His
            180                 185                 190

Ser Ser Val Glu Arg Ala Gly Leu Ile Gly Gly Val Lys Leu Lys Ala
    195                 200                 205

Ile Pro Ser Asp Gly Lys Phe Ala Met Arg Ala Ser Ala Leu Gln Glu
210                 215                 220

Ala Leu Glu Arg Asp Lys Ala Ala Gly Leu Ile Pro Phe Phe Val Val
225                 230                 235                 240

Ala Thr Leu Gly Thr Thr Ser Cys Cys Ser Phe Asp Asn Leu Leu Glu
                245                 250                 255

Val Gly Pro Ile Cys His Glu Glu Asp Ile Trp Leu His Val Asp Ala
            260                 265                 270

Ala Tyr Ala Gly Ser Ala Phe Ile Cys Pro Glu Phe Arg His Leu Leu
    275                 280                 285

Asn Gly Val Glu Phe Ala Asp Ser Phe Asn Phe Asn Pro His Lys Trp
290                 295                 300

Leu Leu Val Asn Phe Asp Cys Ser Ala Met Trp Val Lys Arg Arg Thr
305                 310                 315                 320

Asp Leu Thr Gly Ala Phe Lys Leu Asp Pro Val Tyr Leu Lys His Ser
                325                 330                 335

```
His Gln Gly Ser Gly Leu Ile Thr Asp Tyr Arg His Trp Gln Leu Pro
            340                 345                 350
Leu Gly Arg Arg Phe Arg Ser Leu Lys Met Trp Phe Val Phe Arg Met
            355                 360                 365
Tyr Gly Val Lys Gly Leu Gln Ala Tyr Ile Arg Lys His Val Gln Leu
        370                 375                 380
Ser His Glu Phe Glu Ala Phe Val Leu Gln Asp Pro Arg Phe Glu Val
385                 390                 395                 400
Cys Ala Glu Val Thr Leu Gly Leu Val Cys Phe Arg Leu Lys Gly Ser
                405                 410                 415
Asp Gly Leu Asn Glu Ala Leu Leu Glu Arg Ile Asn Ser Ala Arg Lys
            420                 425                 430
Ile His Leu Val Pro Cys Arg Leu Arg Gly Gln Phe Val Leu Arg Phe
            435                 440                 445
Ala Ile Cys Ser Arg Lys Val Glu Ser Gly His Val Arg Leu Ala Trp
        450                 455                 460
Glu His Ile Arg Gly Leu Ala Ala Glu Leu Leu Ala Ala Glu Glu Gly
465                 470                 475                 480
Lys Ala Glu Ile Lys Ser
                485

<210> SEQ ID NO 7
<211> LENGTH: 1859
<212> TYPE: DNA
<213> ORGANISM: Sus scrofa

<400> SEQUENCE: 7
gaattcacat atgaatgcca gcgatttccg tcgacgcggc aaagaaatgg tggattacat      60
ggcggattac ctggaaggca tcgaaggtcg tcaggtgtac ccggatgtgc agccggggta     120
cctgcgtccg ctgatcccgg cgaccgcccc gcaggaaccg gataccttcg aagatatcct     180
gcaggatgtg gaaaaaatca tcatgccggg ggtgacccac tggcacagcc gtacttctt      240 cgcgtacttc ccgaccgcca gcagctaccg ggcgatgctg gcggatatgc gtgcggtgc      300 gatcggatgc atcggttttca gctgggcggc tagcccggcg tgcaccgaac tcgagaccgt     360
gatgatggat tggctgggca aaatgctcca gcttccggaa gcgttcctgg cgggcgaagc     420
cggtgaaggc ggcggcgtga tccagggtag cgccagcgaa gccaccctgg tggcgctgct     480
ggcggcgcgt accaaagtgg tgcgacgtct gcaagcggcg agcccgggcc tgacccaggg     540
cgcggtgctg gaaaaactag tggcgtacgc gagtgatcag gcgcacagca gcgtggaacg     600
tgccggcctg atcggcggcg tgaaactgaa agcgatcccg agcgatggca aattcgcgat     660
gcgtgcgagc gcgctgcagg aggccctgga gagagacaag gctgccggcc tgattccttt     720
cttcgtggtg gctacgctgg ggaccacatc gtgctgctcc tttgacaatc tcttagaagt     780
gggacccatc tgtcacgaag aggacatatg gctgcacgtg gatgctgcct acgcaggcag     840
tgccttcatc tgccctgagt tccggcacct gctgaatgga gtggagtttg cagattcatt     900
taactttaat ccccacaaat ggctcttggt gaattttgac tgctcggcta tgtgggtgaa     960
aaggagaacg gacctgactg gagccttcaa attggacccc gtgtacttaa gcacagcca    1020 ccagggctcg gggcttatca cggactacag gcactggcag ctgccactgg gtcggcgatt    1080
ccggtccctg aaaatgtggt ttgtttttag gatgtacgga gtcaagggac tgcaggccta    1140
tatccgcaag cacgtgcagc tgtctcatga gtttgaggca tttgtgcttc aggatccacg    1200
```

-continued

| | |
|---|---|
| ctttgaagtc tgtgccgaag tcaccctggg gctggtgtgt ttccggctga agggctccga | 1260 |
| cggactgaat gaagcgcttc tggaaaggat aaacagcgcc aggaaaatcc acttggttcc | 1320 |
| ctgtcgcctg aggggccagt tcgtgctgcg gttcgccatc tgctcgcgca aggtggagtc | 1380 |
| gggccacgtg cggctggcct gggagcacat ccgagggctg gcggccgagc tgctggccgc | 1440 |
| ggaggaggga aaggcagaga tcaaaagttg aagtgccctg aagagcagaa tcggaggaga | 1500 |
| cgcgtcgtcc ccgctccgag gcgtagagcc tgcaatggtc cccccagttc tttagcccac | 1560 |
| gttctccaga aagaagcttg tgcctacgtc tgaccagcct ctcagcaatg aagaagtatt | 1620 |
| atttgctctt tgaaaagtta atcccagtgg agacagcttt tactctttat ttggctgtga | 1680 |
| ttgtttgttg attaaaacat cataggtttc tgcatccttg aagttgtcag cggtggtcca | 1740 |
| ctttccgggg caacctatgc tgatgggatt tgagatgata cccgtggtct ttaaattact | 1800 |
| ctgtcctgtg gcttatgctt aataaatgat gtgaagtgta aaaaaaaaa aaaaaaaa | 1859 |

<210> SEQ ID NO 8
<211> LENGTH: 510
<212> TYPE: PRT
<213> ORGANISM: Micrococcus luteus

<400> SEQUENCE: 8

Met Thr Thr Ala Pro Ala Thr Gly Arg Glu Arg Arg Thr Ser Asp
1               5                   10                  15

Val Val Val Ile Gly Ala Gly Pro Ala Gly Leu Met Ala Ala Arg Thr
            20                  25                  30

Ala Lys Ala Gln Gly Leu Ser Val Thr Val Leu Glu Ala Arg Arg Arg
        35                  40                  45

Val Gly Gly Arg Thr Trp Asn Gly Leu Val Glu Gly Ala Asp Gly Lys
    50                  55                  60

Asp His Phe Ile Glu Ile Gly Gly Gln Trp Ile Ser Pro Asp Gln Thr
65                  70                  75                  80

Arg Leu Ile Ser Leu Val Glu Glu Leu Gly Leu Pro Thr Phe Ser Arg
                85                  90                  95

Phe Arg Asp Gly Arg Asn Val Tyr Val Asp Pro Arg Gly Glu Arg His
            100                 105                 110

Val Tyr Asp Gly Leu Asp Phe Pro Val Ala Glu Lys Thr Asp Arg Glu
        115                 120                 125

Met Asp Arg Leu Ile Ala Lys Ile Asp Glu Leu Thr Ala Glu Ile Asp
    130                 135                 140

Ala Ala Ala Pro Trp Glu His Pro Arg Ala Ala Glu Leu Asp Thr Ile
145                 150                 155                 160

Ser Phe Arg His Trp Leu Glu Gln Glu Ser Asp Asp Pro Glu Ala Ile
                165                 170                 175

Asp Asn Val Ser Ile Tyr Ile Ala Ser Gly Met Leu Thr Lys Pro Ser
            180                 185                 190

His Thr Phe Ser Met Leu Gln Ala Leu Leu Met Ala Ala Ser Ala Gly
        195                 200                 205

Ser Phe Arg Asn Leu Val Asp Glu Asp Phe Ile Leu Asp Lys Arg Val
    210                 215                 220

Glu Gly Gly Met Gln Ser Val Ser Leu Thr Met Ala Ala Glu Leu Gly
225                 230                 235                 240

Asp Asp Val Val Leu Gly Gln Pro Val Arg Thr Leu Arg Trp Ala Glu
                245                 250                 255

Pro Asp Pro Ser Thr Ala Asp Glu Lys Asn Gly Val Ala Ala Asp Val

```
                    260                 265                 270
Arg Asn Gly Val Ala His Asp Gly Ala Ala Gly Asp Val Val Ala Leu
        275                 280                 285

Thr Asp Asp Tyr Glu Val His Ala Arg Tyr Ala Val Leu Ala Val Pro
        290                 295                 300

Pro Asn Leu Tyr Ser Arg Ile Ser Phe Glu Pro Pro Met Pro Arg Glu
305                 310                 315                 320

Gln Gln Ile Ala His Gln His Ile Ser Met Gly Leu Val Ile Lys Val
                325                 330                 335

His Ala Val Tyr Glu Thr Pro Phe Trp Arg Glu Glu Gly Leu Ser Gly
                340                 345                 350

Thr Cys Phe Gly Gly Gly Arg Leu Val Gln Glu Ile Tyr Asp Asn Thr
        355                 360                 365

Asn Arg Gly Glu Asn Leu Ala Gly Gly Ala Pro Gly Glu Glu Asp Pro
        370                 375                 380

His Gly Thr Leu Val Gly Phe Val Ser Asp Val Tyr Ala Glu Gln Met
385                 390                 395                 400

Trp Ala Leu Pro Glu Glu Glu Arg Lys Ala Ala Ile Leu Gly Ala Met
                405                 410                 415

Ala Glu Tyr Leu Gly Pro Arg Thr Leu Glu Pro Ile Ala Phe Phe Leu
                420                 425                 430

Ser Asp Met Ala Ala Glu Glu Trp Thr Arg Gly Ala Tyr Ala Thr Ser
        435                 440                 445

Tyr Asp Leu Gly Gly Leu Ser Arg Trp Gly His Leu Gln Asn Arg Pro
        450                 455                 460

Thr Gly Pro Ile His Tyr Ala Cys Ser Asp Ile Ala Ala Glu Gly Tyr
465                 470                 475                 480

Gln His Val Asp Gly Ala Ile Arg Met Gly Ala Ala Ala Leu Ala
                485                 490                 495

Ile Ala Glu Arg Glu Ala Thr Asp Ala Gly Gln Pro Thr Gly
                500                 505                 510
```